(12) United States Patent
Wheelan et al.

(10) Patent No.: US 12,263,010 B2
(45) Date of Patent: *Apr. 1, 2025

(54) OPIOID OVERDOSE ALERT WEARABLE DEVICE METHOD AND DEVICES

(71) Applicant: GJN INTERNATIONAL LLC, Cherry Hill, NJ (US)

(72) Inventors: Renaya Furtick Wheelan, Cherry Hill, NJ (US); Scott Shanks, Byrn Mawr, PA (US)

(73) Assignee: GJN International LLC, Cherry Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,184

(22) Filed: Aug. 11, 2023

(65) Prior Publication Data

US 2023/0380761 A1 Nov. 30, 2023

Related U.S. Application Data

(63) Continuation of application No. 17/827,735, filed on May 29, 2022, now Pat. No. 11,723,593.

(51) Int. Cl.
| | |
|---|---|
| *A61B 5/00* | (2006.01) |
| *A61B 5/0205* | (2006.01) |
| *A61B 5/024* | (2006.01) |
| *A61B 5/08* | (2006.01) |
| *A61B 5/11* | (2006.01) |
| *A61B 5/117* | (2016.01) |
| *G16H 15/00* | (2018.01) |
| *H04W 4/02* | (2018.01) |

(52) U.S. Cl.
CPC .......... *A61B 5/4845* (2013.01); *A61B 5/0022* (2013.01); *A61B 5/02055* (2013.01);
(Continued)

(58) Field of Classification Search
CPC ..... A61B 5/0022; A61B 5/01; A61B 5/02055; A61B 5/024; A61B 5/02438; A61B 5/0816; A61B 5/1112; A61B 5/117; A61B 5/4833; A61B 5/4845; A61B 5/681; A61B 5/7282; A61B 5/746; A61B 5/747; G16H 15/00; G16H 20/17; G16H 40/63; G16H 40/67; G16H 50/20; H04W 4/02
(Continued)

(56) References Cited

U.S. PATENT DOCUMENTS

| | | | |
|---|---|---|---|
| 11,723,593 B1 * | 8/2023 | Wheelan | A61B 5/747 |
| | | | 600/301 |
| 2009/0322513 A1 * | 12/2009 | Hwang | H04W 4/90 |
| | | | 600/301 |

(Continued)

*Primary Examiner* — Md K Talukder
(74) *Attorney, Agent, or Firm* — Finnegan, Henderson, Farabow, Garrett & Dunner, LLP

(57) ABSTRACT

The embodiments disclose a method including: monitoring vital signs of an opioid patient, providing chemical identifying and concentration detection of a drug the opioid patient is preparing to inject, analyzing the opioid patient's vital signs to determine an overdose condition regardless of the patient consciousness state, tracking the opioid patient's GPS location, transmitting automatically an overdose emergency alert; sending the automatic opioid overdose emergency alert to the closest first responders, and providing the opioid patient's ID, GPS location, vital signs, potential drug overdosed, and known drug use in the automatic opioid overdose emergency alert to the closest first responders.

20 Claims, 21 Drawing Sheets

(52) U.S. Cl.
CPC ............ *A61B 5/024* (2013.01); *A61B 5/0816* (2013.01); *A61B 5/1112* (2013.01); *A61B 5/117* (2013.01); *A61B 5/681* (2013.01); *A61B 5/746* (2013.01); *G16H 15/00* (2018.01); *H04W 4/02* (2013.01)

(58) Field of Classification Search
USPC ........................................................ 600/301
See application file for complete search history.

(56) References Cited

U.S. PATENT DOCUMENTS

| | | | |
|---|---|---|---|
| 2013/0021154 A1* | 1/2013 | Solomon | G16H 80/00 |
| | | | 340/539.12 |
| 2016/0338642 A1* | 11/2016 | Parara | A61B 5/1112 |
| 2017/0172522 A1* | 6/2017 | Insler | A61B 5/4845 |
| 2017/0188945 A1* | 7/2017 | Lin | A61B 5/742 |
| 2019/0216321 A1* | 7/2019 | Grande | A61B 5/1112 |
| 2019/0271714 A1* | 9/2019 | Kluckner | G01N 21/63 |
| 2019/0374713 A1* | 12/2019 | Kiani | A61B 5/4848 |
| 2020/0000395 A1* | 1/2020 | Ganesan | A61B 5/681 |
| 2020/0121852 A1* | 4/2020 | Winbush | A61B 5/0205 |
| 2020/0352456 A1* | 11/2020 | Joseph | A61B 5/486 |
| 2020/0405226 A1* | 12/2020 | Kiani | G16H 20/13 |
| 2021/0161465 A1* | 6/2021 | Barker | A61B 5/14532 |
| 2022/0330904 A1* | 10/2022 | VanDerKarr | G08B 21/02 |
| 2022/0398914 A1* | 12/2022 | Cardona | G06F 1/163 |
| 2023/0138098 A1* | 5/2023 | Telfort | A61B 5/746 |
| | | | 600/301 |

\* cited by examiner

OPIOID OVERDOSE ALERT WEARABLE DEVICE METHOD AND DEVICES

This Patent Application is a Continuation of the United States Patent Application entitled: "OPIOID OVERDOSE ALERT WEARABLE DEVICE METHOD AND DEVICES", U.S. Ser. No. 17/827,735, filed on May 29, 2022 by Renaya Furtick Wheelan, which is incorporated herein by reference.

BACKGROUND

There has been a war waged on the United States for at least the past 10 years. It's a war that sheds no blood and blows up no buildings. It's a war on the American people. Who are those that have taken the lives of over 700,000 people? China and Mexico have waged a silent war against the American people instead of using guns they use the opioid epidemic to take out countless numbers of the American people. People who are dying alone on cold bathroom floors, in abandoned houses, on park benches, in alleyways, or in their bedrooms each year. According to the Center for Disease Control and Prevention, there were more than 68,000 drug overdose deaths in 2018.

DETAILED DESCRIPTION OF THE INVENTION

In the following description, reference is made to the accompanying drawings, which form a part hereof, and which are shown by way of illustration as a specific example in which the invention may be practiced. It is to be understood that other embodiments may be utilized and structural changes may be made without departing from the scope of the present invention.

General Overview

It should be noted that the descriptions that follow, for example, in terms of an opioid overdose alert wearable device method and devices are described for illustrative purposes and the underlying system can apply to any number and multiple types of drug addictions. In one embodiment of the present invention, the opioid overdose alert wearable device can be configured using physiological sensors to monitor a patient's vital signs 24/7. The opioid overdose alert wearable device can be configured to include cellular connectivity and can be configured to include satellite connectivity using the present invention.

Figure 1:
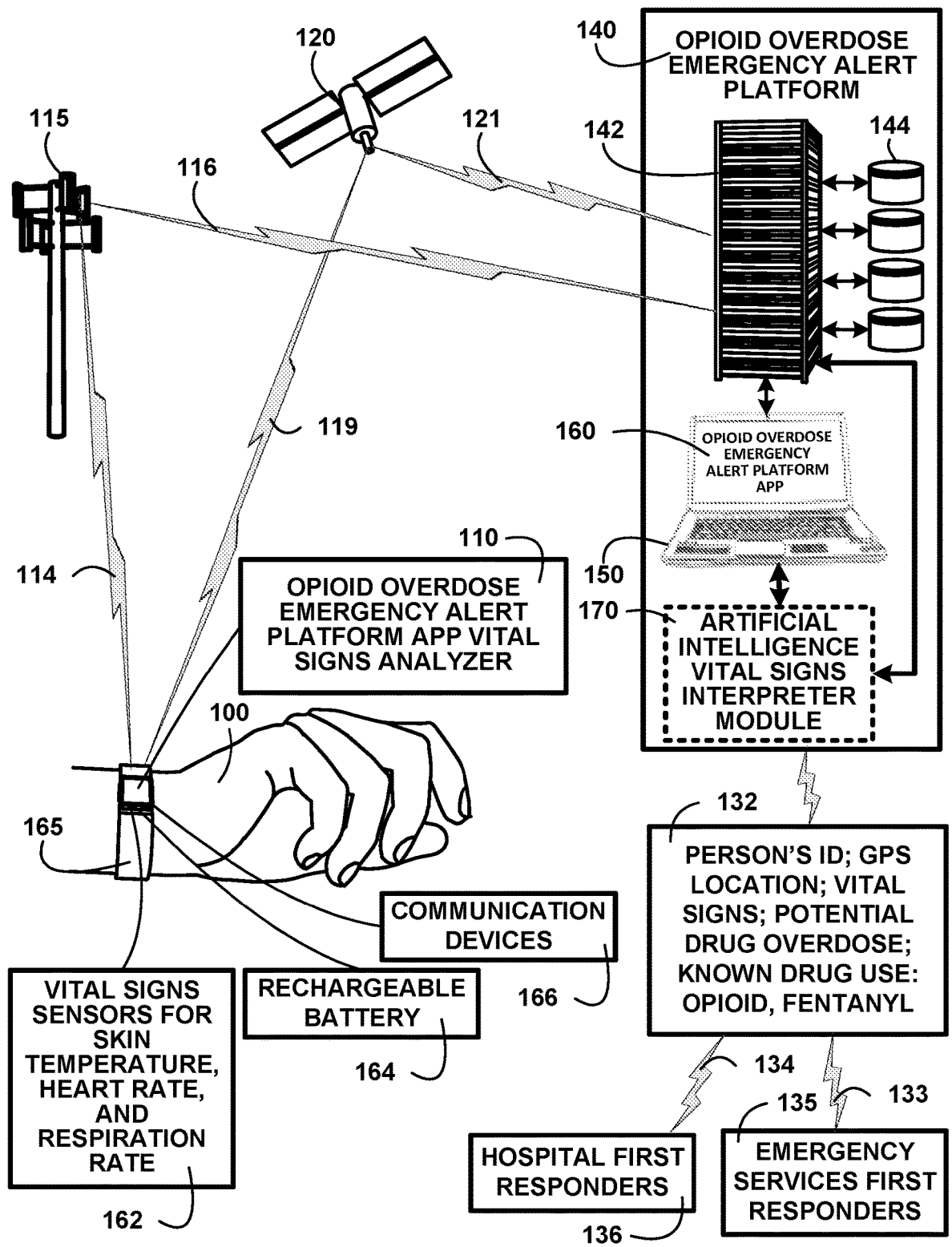
FIG. 1 shows for illustrative purposes only an example of an overview of the opioid overdose emergency alert platform of one embodiment.

FIG. 1 shows for illustrative purposes only an example of an overview of the opioid overdose emergency alert platform of one embodiment. FIG. 1 shows an opioid patient 100 wearing an opioid overdose alert wearable device 165. The opioid overdose alert wearable device 165 includes vital signs sensors for skin temperature, heart rate, and respiration rate 162. A rechargeable battery 164 provides power to opioid overdose alert wearable device 165 vital signs sensors for skin temperature, heart rate, respiration rate 162, and communication devices 166. An opioid overdose emergency alert platform app vital signs analyzer 110 sends a wearable device transmission to a cellular signal 114 via a cellular tower 115. The cellular transmission to an opioid overdose emergency alert platform 116 is performed for storing the data transmitted. If cellular service is not available a wearable device transmission to a satellite 119 is sent to a satellite 120 and the satellite transmission 121 is relayed to the opioid overdose emergency alert platform 140. The opioid overdose emergency alert platform 140 includes a plurality of servers and digital processors 142, a plurality of databases 144, an opioid overdose emergency alert platform app 160 on a platform computer 150, and an artificial intelligence vital signs interpreter module 170. The opioid overdose alert wearable device 165 transmissions include the person's ID; GPS location; vital signs; potential drug overdose; known drug use: opioid, fentanyl 132 in an alert signal 134 to hospital first responders 136 and a simultaneous alert signal 133 to emergency services first responders 135. The purpose of the simultaneous alert signal 133 is to get lifesaving medical attention to the patient quickly whose vital signs are indicating an overdose condition.

Detailed Description

Figure 2:
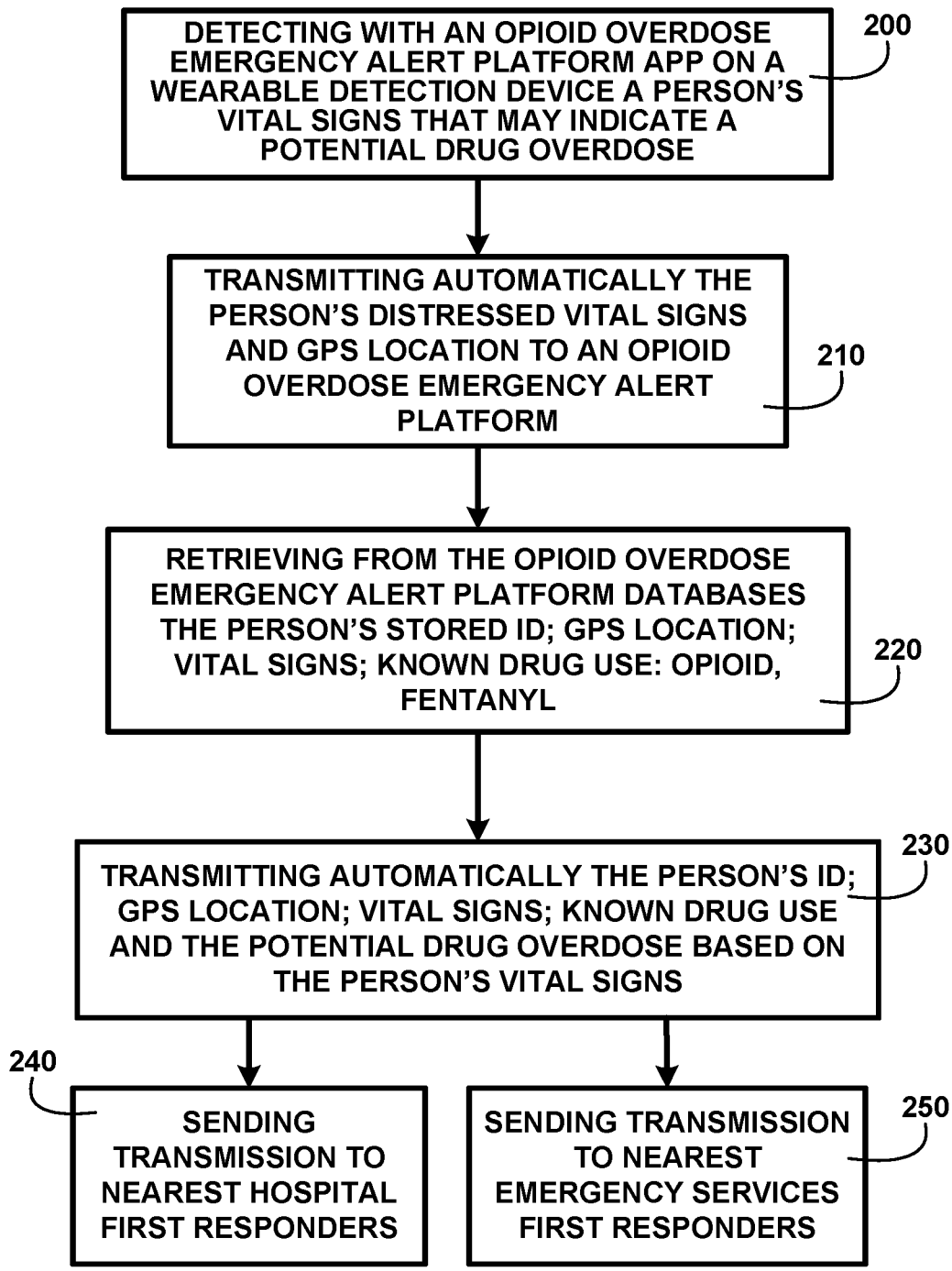
FIG. 2 shows a block diagram of an overview flow chart of detecting a person's vital signs of one embodiment.

FIG. 2 shows a block diagram of an overview flow chart of detecting a person's vital signs of one embodiment. FIG. 2 shows detecting with an opioid overdose emergency alert platform app on a wearable detection device a person's vital signs that may indicate a potential drug overdose 200. Transmitting automatically the person's distressed vital signs and GPS location to an opioid overdose emergency alert platform 210. Retrieving from the opioid overdose emergency alert platform databases the person's stored id; GPS location; vital signs; known drug use: opioid, fentanyl 220. Transmitting automatically the person's id; GPS location; vital signs; known drug use and the potential drug overdose based on the person's vital signs 230. Sending transmission to nearest hospital first responders 240. Sending transmission to nearest emergency services first responders 250 of one embodiment.

Figure 3A:
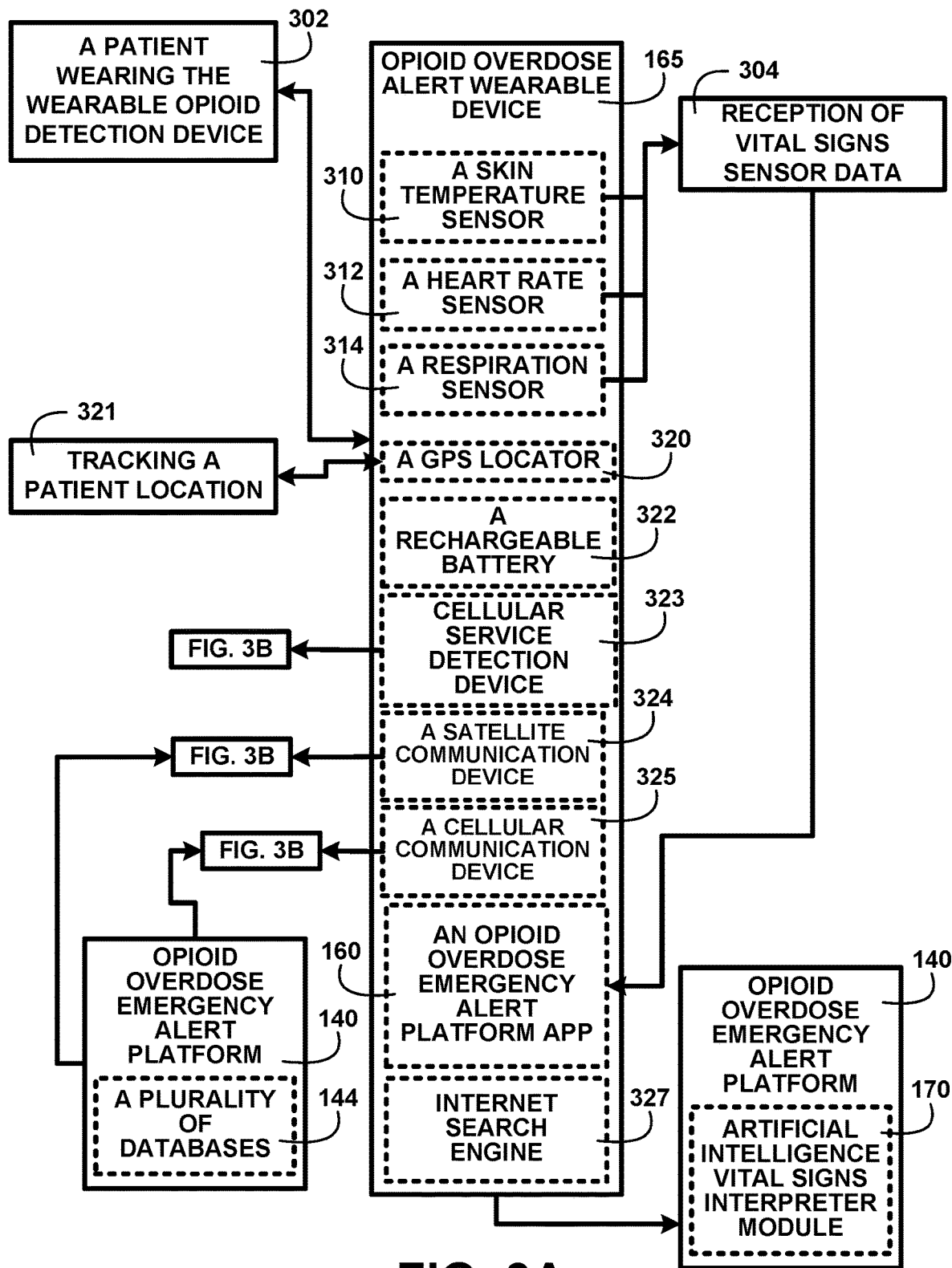
FIG. 3A shows a block diagram of an overview of a wearable opioid detection device of one embodiment.

A Wearable Opioid Detection Device:

FIG. 3A shows a block diagram of an overview of a wearable opioid detection device of one embodiment. FIG. 3A shows the opioid overdose alert wearable device 165. A patient wearing the wearable opioid detection device 302 produces the reception of vital signs sensor data 304 on the opioid overdose alert wearable device 165, an opioid overdose emergency alert platform app 160, and opioid overdose emergency alert platform 140. Vital signs are detected and measured with a skin temperature sensor 310, a heart rate sensor 312, and a respiration sensor 314. The opioid overdose alert wearable device 165 also detects with a GPS locator 320 for tracking a patient location 321. A rechargeable battery 322 powers the sensors and electronic devices. A cellular service detection device 323 is used to detect the availability of cellular service. The description continues in FIG. 3B. Communications and alerts can be accomplished with a satellite communication device 324 with descriptions continued in FIG. 3B.

Figure 3B:
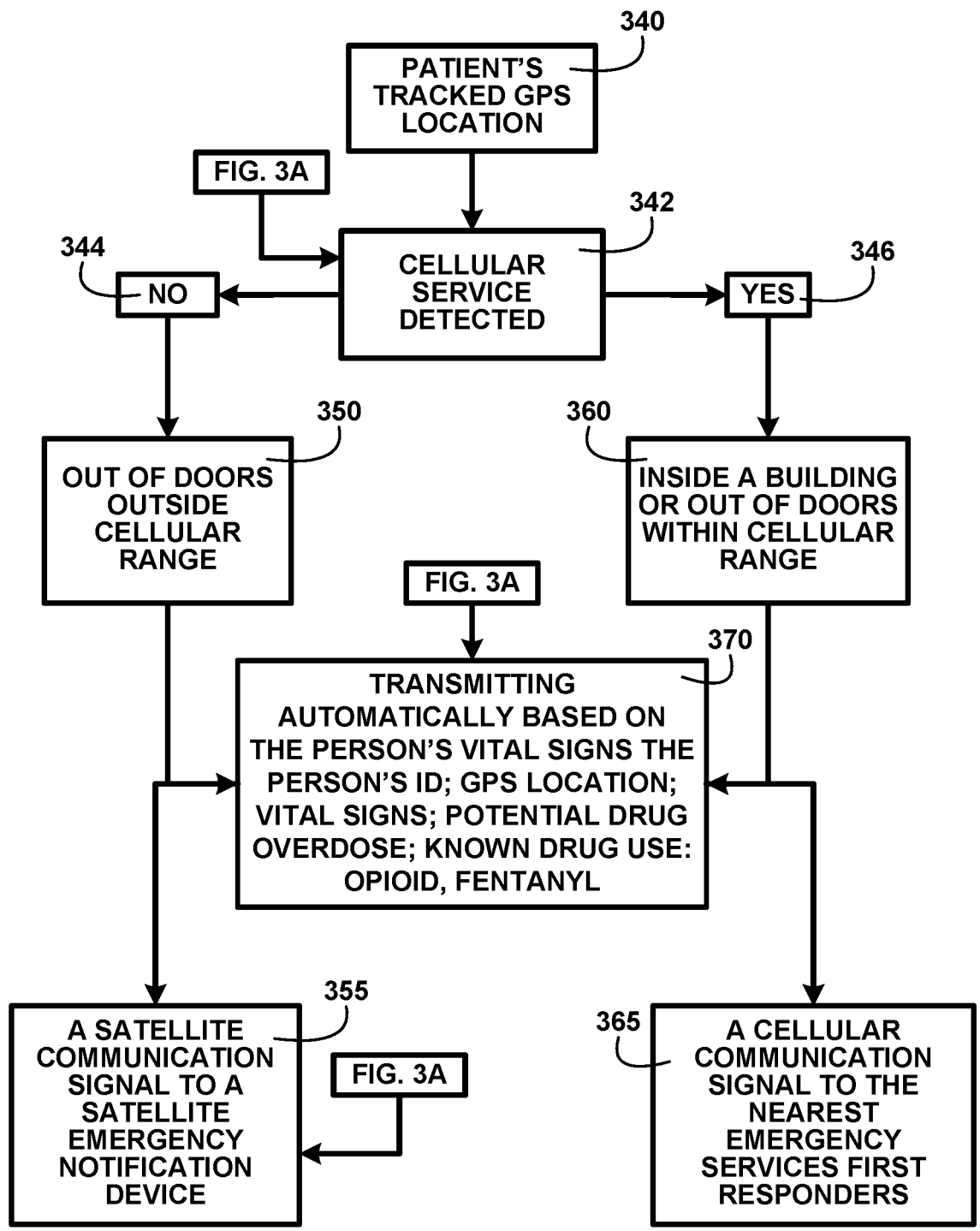
FIG. 3B shows a block diagram of an overview of the patient's tracked GPS location of one embodiment.

Communications and alerts can be accomplished with a cellular communication device 325 with descriptions continued in FIG. 3B. An opioid overdose emergency alert platform app 160 wirelessly coupled to an opioid overdose emergency alert platform 140. The opioid overdose emergency alert platform 140 includes a plurality of databases 144, and an internet search engine 327. The opioid overdose emergency alert platform 140 includes an artificial intelligence vital signs interpreter module 170 of one embodiment.

Patient's Tracked GPS Location:

FIG. 3B shows a block diagram of an overview of the patient's tracked GPS location of one embodiment. FIG. 3B shows a continuation from FIG. 3A. The patient's tracked GPS location 340 requires a GPS coordinate source from for example, a cellular service detected 342. A patient may be out of doors for example, hiking and outside of cellular service range. The opioid overdose alert wearable device 165 includes the cellular service detection device 323. If the response from the cellular service detection device 323 is no 344 because the patient is out of doors outside cellular range 350. If the response from the cellular service detection device 323 is yes 346 because the patient is inside a building or out of doors within cellular range 360.

The opioid overdose alert wearable device 165 is transmitting automatically the person's ID; GPS location; vital signs; potential drug overdose; known drug use: opioid, fentanyl 370 based on the person's vital signs. Based on no response from the cellular service detection device 323 the opioid overdose alert wearable device 165 can transmit a satellite communication signal to a satellite emergency notification device 355. If cellular service is available, the opioid overdose alert wearable device 165 will transmit a cellular communication signal to the nearest emergency services first responders 365 of one embodiment.

The display of the opioid overdose alert wearable device 165 GPS locator 320 includes a location map showing streets and nearby businesses and buildings. This allows medical staff, friends, and family to find the patient more easily in an overdose condition. It further provides medical staff, friends, and family an idea of the patient's frequented sites that may reflect past hangouts when the patient was at the height of drug use. The opioid overdose alert wearable device 165 expands its benefits by alerting those providing help when the patient goes into an overdose condition, without patient action. Repeating past behavior actions may lead to the patient increasing their drug use and increasing their chance of an overdose. The medical staff, friends, and family may be able to counsel the patient on the dangers of repeating the past and further help the patient by preventing situations that would lead to an overdose condition.

Figure 4A:
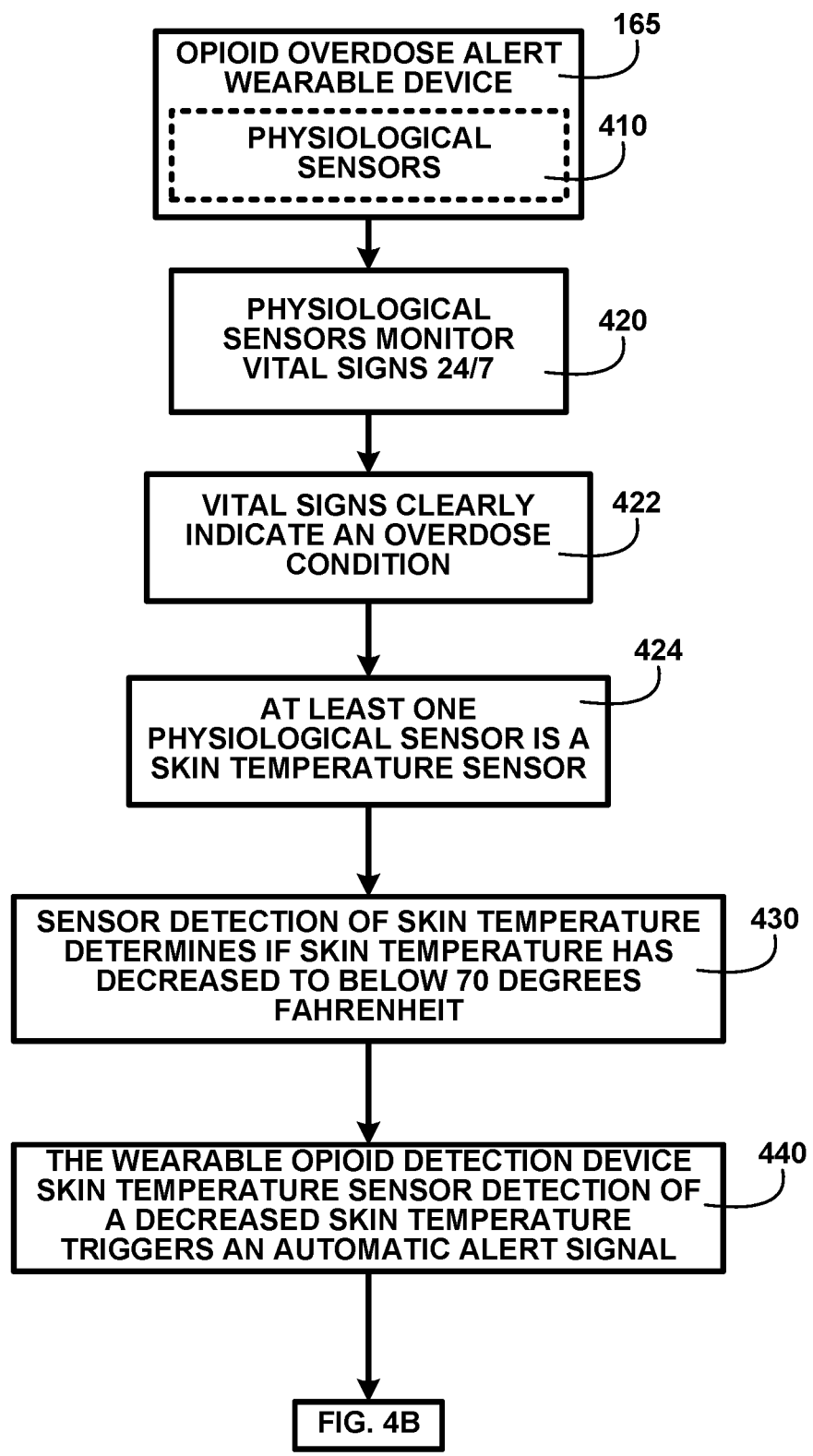
FIG. 4A shows a block diagram of an overview of physiological sensors of one embodiment.

Physiological Sensors:

FIG. 4A shows a block diagram of an overview of physiological sensors of one embodiment. FIG. 4A shows an opioid overdose alert wearable device 165 with physiological sensors 410. The physiological sensors monitor vital signs 24/7 420. Vital signs clearly indicate an overdose condition 422. At least one physiological sensor is a skin temperature sensor 424. Sensor detection of skin temperature determines if skin temperature has decreased to below 70 degrees Fahrenheit 430. The wearable opioid detection device skin temperature sensor detection of a decreased skin temperature triggers an automatic alert signal 440. The descriptions continue in FIG. 4B of one embodiment.

Figure 4B:
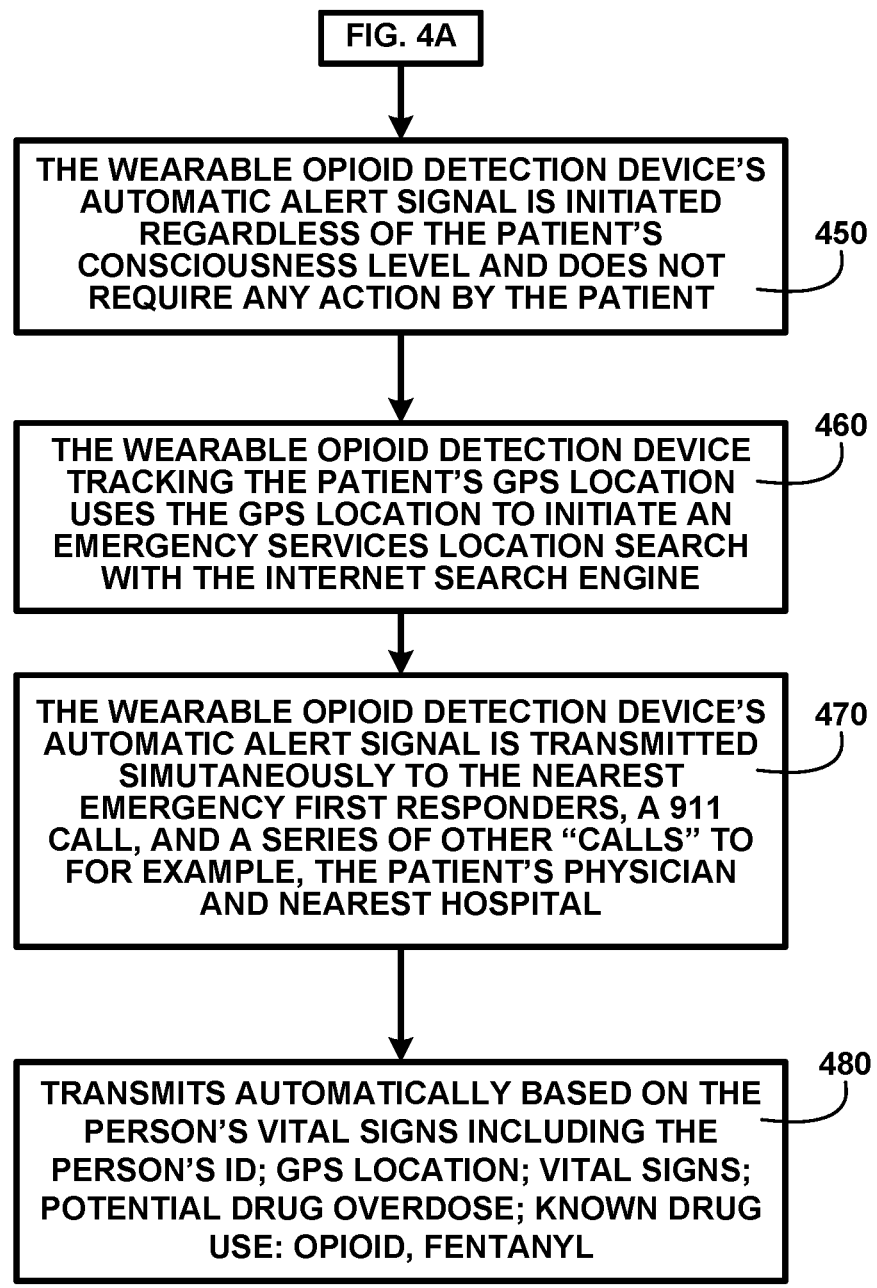
FIG. 4B shows a block diagram of an overview of the detection device automatic alert signal of one embodiment.

Detection Device Automatic Alert Signal:

FIG. 4B shows a block diagram of an overview of the detection device automatic alert signal of one embodiment. FIG. 4B shows a continuation from FIG. 4A. The wearable opioid detection device's automatic alert signal is initiated regardless of the patient's consciousness level and does not require any action by the patient 450. The wearable opioid detection device tracking the patient's GPS location uses the GPS location to initiate an emergency services location search with the internet search engine 460. The wearable opioid detection device's automatic alert signal is transmitted simultaneously to the nearest emergency first responders, a 911 call, and a series of other "calls" to for example, the patient's physician and nearest hospital 470. The alert signal transmits automatically based on the person's vital signs including the person's ID; GPS location; vital signs; potential drug overdose; known drug use: opioid, fentanyl 480 of one embodiment.

Figure 5A:
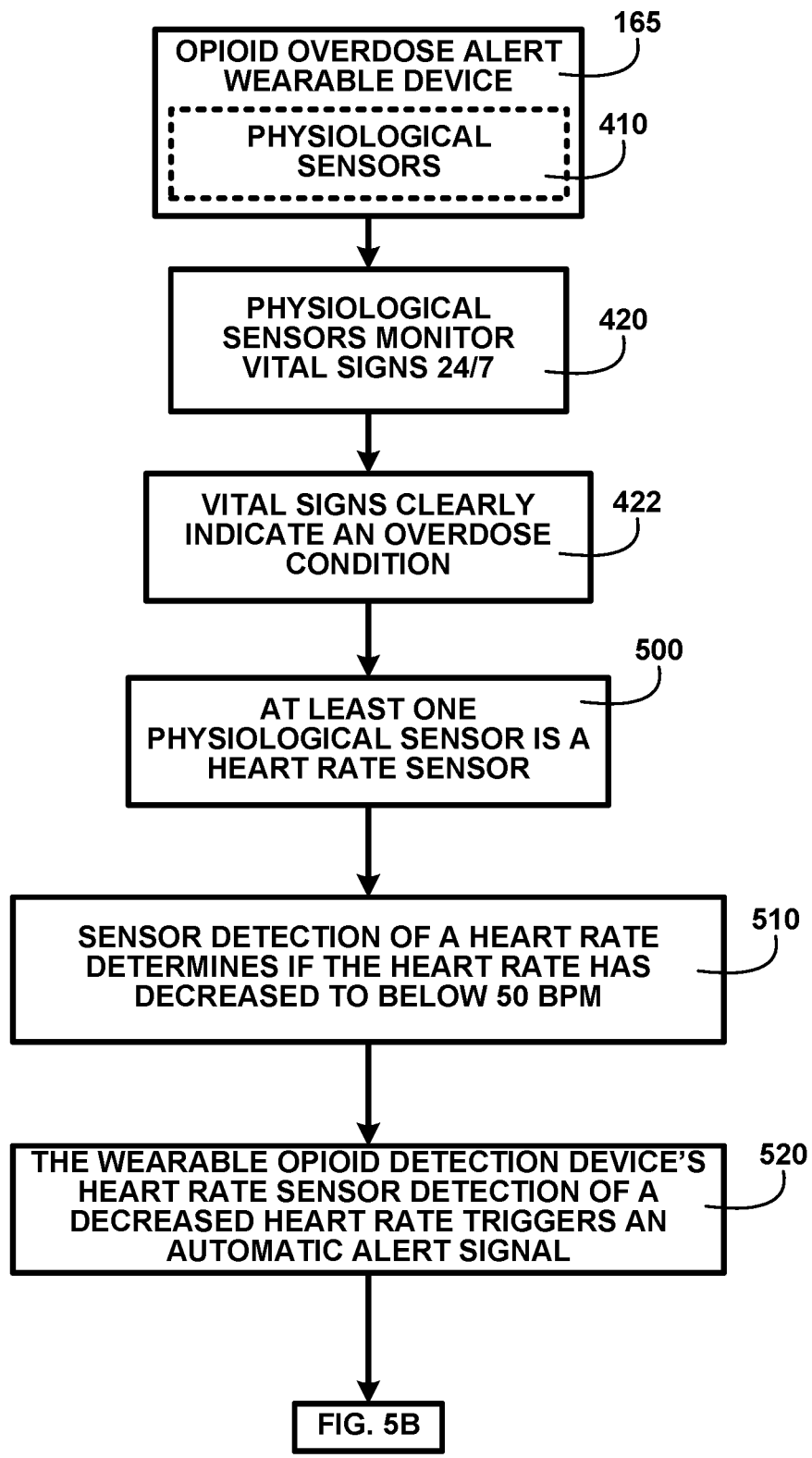
FIG. 5A shows a block diagram of an overview of physiological sensors monitoring vital signs 24/7 of one embodiment.

Physiological Sensors Monitor Vital Skins 24/7:

FIG. 5A shows a block diagram of an overview of physiological sensors monitoring vital signs 24/7 of one embodiment. FIG. 5A shows the opioid overdose alert wearable device 165 with physiological sensors 410. The physiological sensors monitor vital signs 24/7 420. Vital signs clearly indicate an overdose condition 422. At least one physiological sensor is a heart rate sensor 500. The heart rate sensor detection of a heart rate determines if the heart rate has decreased to below 50 bpm 510. The wearable opioid detection device's heart rate sensor detection of a decreased heart rate triggers an automatic alert signal 520. The descriptions continue in FIG. 5B of one embodiment.

Figure 5B:
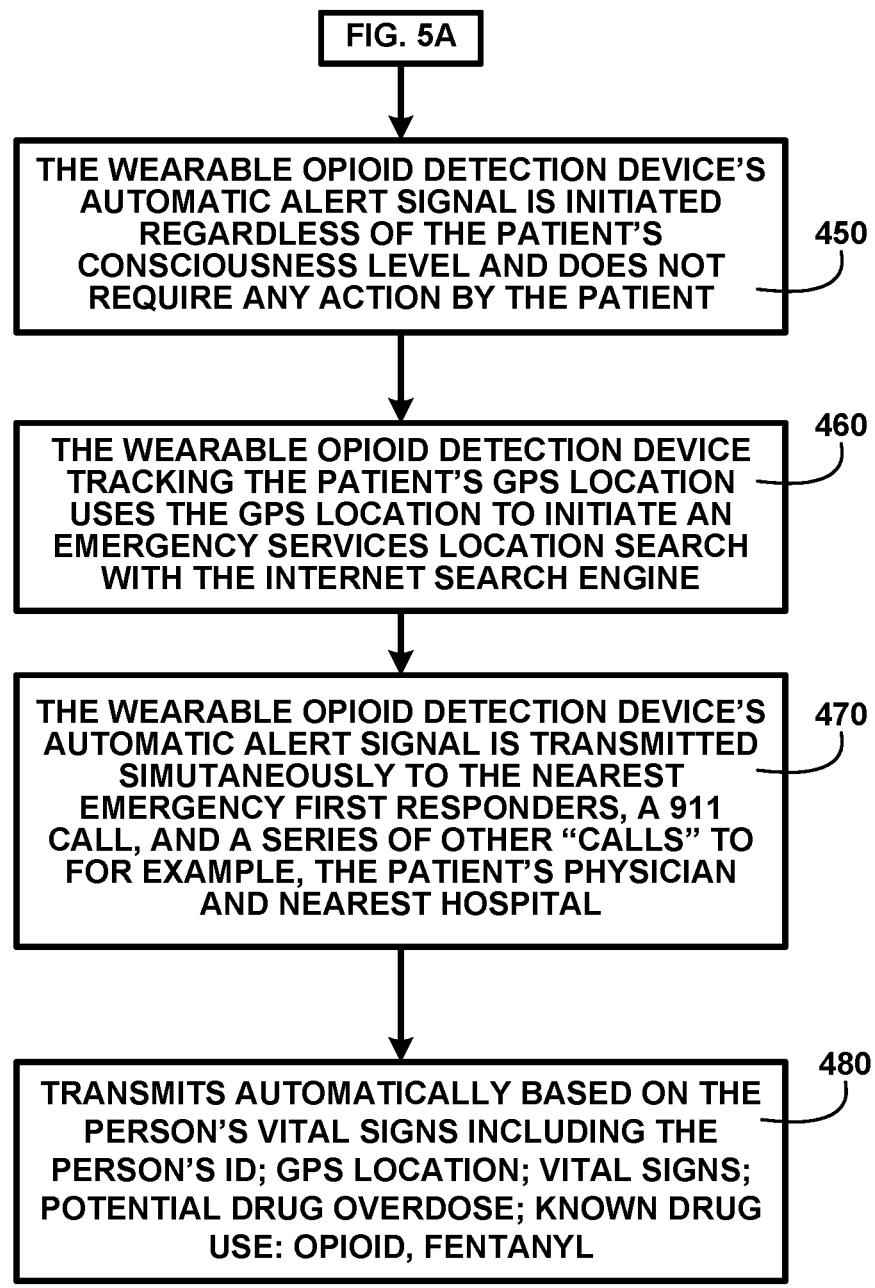
FIG. 5B shows a block diagram of an overview of tracking of the patient's GPS location of one embodiment.

Tracking of the Patient GPS Location:

FIG. 5B shows a block diagram of an overview of tracking of the patient's GPS location of one embodiment. FIG. 5B shows a continuation from FIG. 5A. The wearable opioid detection device's automatic alert signal is initiated regardless of the patient's consciousness level and does not require any action by the patient 450. The wearable opioid detection device tracking the patient's GPS location uses the GPS location to initiate an emergency services location search with the internet search engine 460. The wearable opioid detection device's automatic alert signal is transmitted simultaneously to the nearest emergency first responders, a 911 call, and a series of other "calls" to for example, the patient's physician and nearest hospital 470. The alert signal transmits automatically based on the person's vital signs including the person's ID; GPS location; vital signs; potential drug overdose; known drug use: opioid, fentanyl 480 of one embodiment.

Figure 6A:
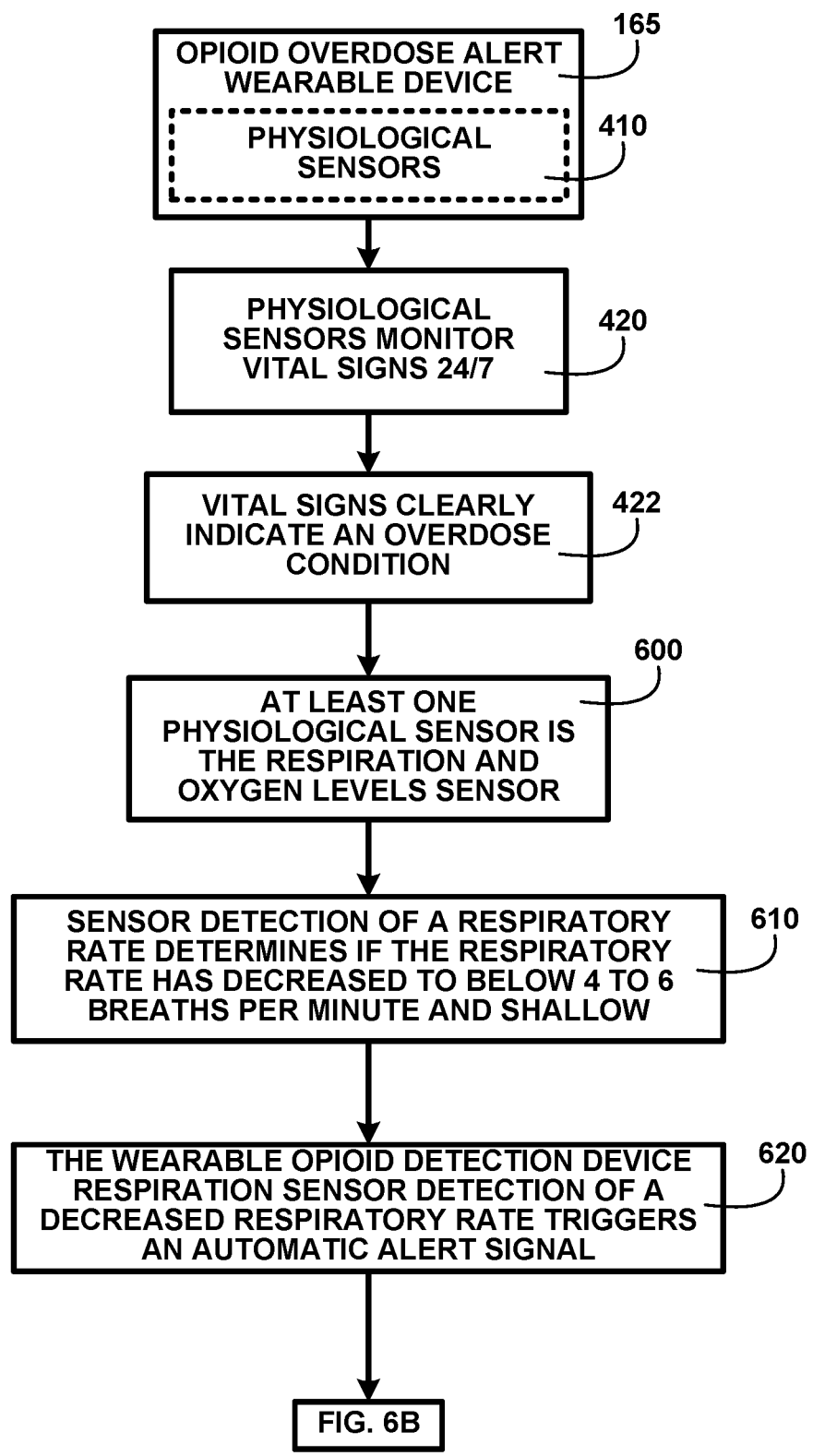
FIG. 6A shows a block diagram of an overview of the respiration sensor of one embodiment.

Respiration Sensor:

FIG. 6A shows a block diagram of an overview of the respiration sensor of one embodiment. FIG. 6A shows an opioid overdose alert wearable device 165 with physiological sensors 410. The physiological sensors monitor vital signs 24/7 420. Vital signs continuously being monitored also provide medical staff the knowledge to note changes in vital signs that may indicate other health conditions that are dangerous for example, heart conditions that may have been initiated by the drug use. Drug use patients are just as susceptible to other critical health conditions as others. Vital signs clearly indicate an overdose condition 422. At least one physiological sensor is the respiration and oxygen levels sensor 600. The sensor detection of a respiratory rate determines if the respiratory rate has decreased to below 4 to 6 breaths per minute and shallow 610. The wearable opioid detection device respiration sensor detection of a decreased respiratory rate triggers an automatic alert signal 620. The description continues in FIG. 6B of one embodiment. In another embodiment, the analysis of vital signs may be expanded to cover other health conditions to broaden the benefits of the opioid overdose alert wearable device 165.

Figure 6B:
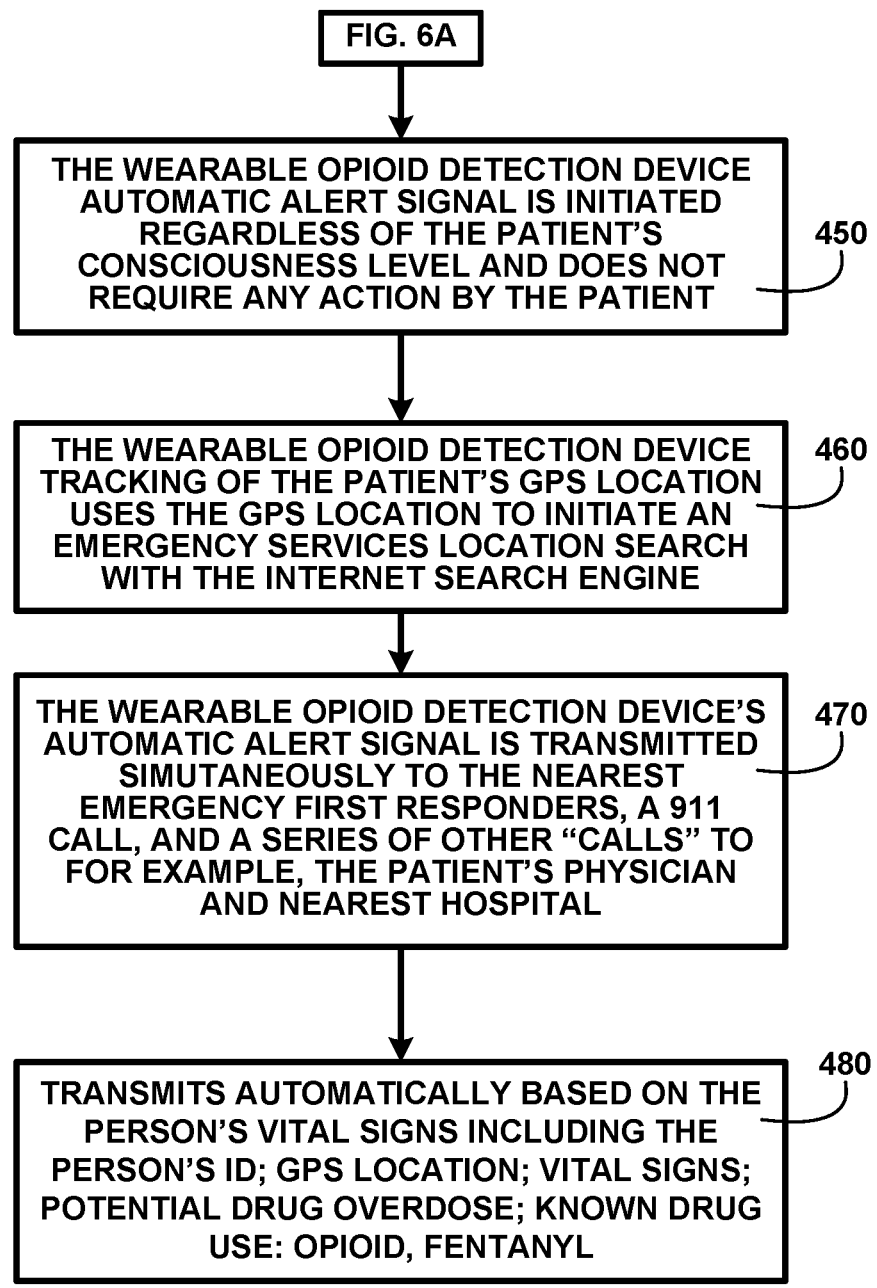
FIG. 6B shows a block diagram of an overview of transmitted simultaneously to the nearest emergency first responders of one embodiment.

Transmitted Simultaneously to the Nearest Emergency First Responders:

FIG. 6B shows a block diagram of an overview of transmitted simultaneously to the nearest emergency first responders of one embodiment. FIG. 6B shows a continuation from FIG. 6A showing the wearable opioid detection device automatic alert signal is initiated regardless of the patient's consciousness level and does not require any action by the patient 450. The wearable opioid detection device tracking of the patient's GPS location uses the GPS location to initiate an emergency services location search with the internet search engine 460. The wearable opioid detection device's automatic alert signal is transmitted simultaneously to the nearest emergency first responders, a 911 call, and a series of other "calls" to for example, the patient's physician and nearest hospital 470. The alert signal transmits automatically based on the person's vital signs including the person's ID; GPS location; vital signs; potential drug overdose; known drug use: opioid, fentanyl 480 of one embodiment.

Figure 7A:
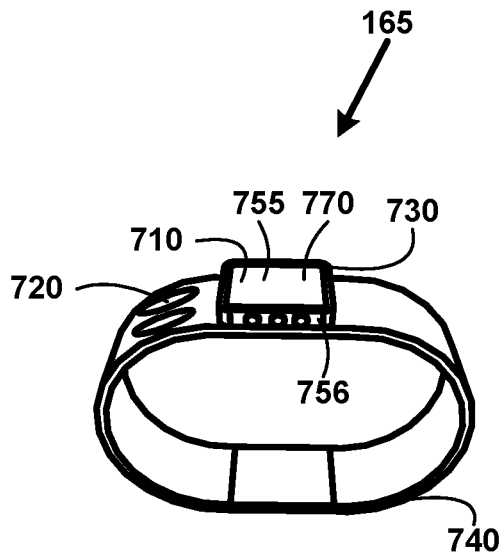
FIG. 7A shows for illustrative purposes only an example of a wearable wristband of one embodiment.

Wearable Wristband:

FIG. 7A shows for illustrative purposes only an example of a wearable wristband of one embodiment. FIG. 7A shows an opioid overdose alert wearable device 165 in a wrist band 740 including a vital signs detector 730, a vital signs display, drug ID, and concentration display 710 and sensor displays 720, includes physiological sensors 755, and at least one communication device 770 of one embodiment. The wristband may be made with a variety of materials and colors to appeal to a patient. The wristband may be made with adjustable stretchable materials.

Figure 7B:
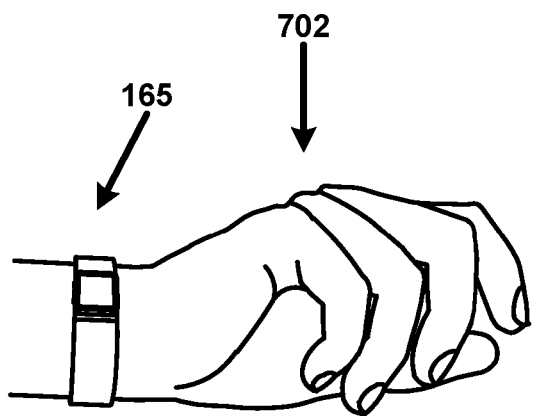
FIG. 7B shows for illustrative purposes only an example of a user wearing a wristband of one embodiment.

User Wearing Wrist Band:

FIG. 7B shows for illustrative purposes only an example of a user wearing the wristband of one embodiment. FIG. 7B shows a patient hand 702 wearing an opioid overdose alert wearable device 165 of one embodiment. The patient-user can wear an opioid overdose alert wearable device 165 just as they would a wristwatch. The opioid overdose alert wearable device 165 is purposely made to not look expensive to reduce the risk of theft. The opioid overdose alert wearable device 165 components are sealed to prevent damage by incidental exposure to a moderate amount of water including rain and even a patient-user taking a shower.

Figure 7C:
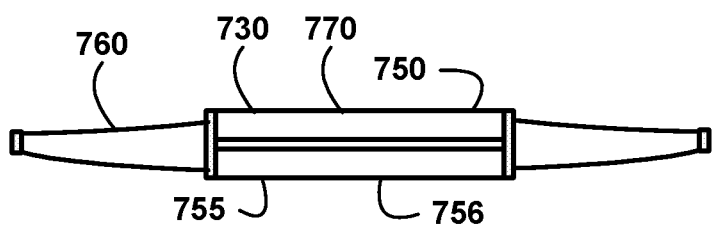
FIG. 7C shows for illustrative purposes only an example of a hair tie wearable device of one embodiment.

Hair Tie Wearable Device:

FIG. 7C shows for illustrative purposes only an example of a hair tie wearable device of one embodiment. FIG. 7C shows a wearable opioid detection hair tie device 750. The wearable device's vital signs detector 730 includes physiological sensors 755 embedded in the hair barrette provide the patient's vital signs monitoring. At least one communication device 770 embedded into the barrette provides the opioid overdose emergency alert platform app 160 of FIG. 1 with connectivity for transmitting alerts and data to the opioid overdose emergency alert platform 140 of FIG. 1. A rechargeable battery 756 embedded in the barrette is the power source for the sensors, communication devices, and other electronics. The elastic locking clip 760 is flexible and stretchable allowing the patient to lock the hair tie in place of one embodiment.

Figure 7D:
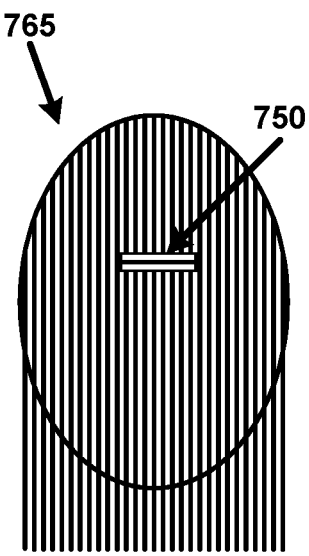
FIG. 7D shows for illustrative purposes only an example of a user wearing a hair tie of one embodiment.

User Wearing Hair Tie:

FIG. 7D shows for illustrative purposes only an example of a user wearing a hair tie of one embodiment. FIG. 7D shows a patient's back view of long hair 765. A wearable opioid detection hair tie device 750 attached to the patient's hair provides the patient's vital signs monitoring and tracking the patient location. The hair tie embodiment also hides the purpose of the device and resembles a typical hair barrette to reduce presenting something of value potentially the subject of theft of one embodiment.

Upon first glance, the wearable opioid detection hair tie device may appear to be insufficient to provide all the features of the opioid overdose alert wearable device 165. However, that is not the case. All the features of the opioid overdose alert wearable device 165 are incorporated in the wearable opioid detection hair tie device albeit in a different configuration. The wearable opioid detection hair tie device provides an alternative that those patients used to wearing a wristwatch may find less disruptive to their current routine. Even those who have shortened hair may choose to use the wearable opioid detection hair tie device and simply wear for example, a baseball cap to cover it. A cap will not interfere with the functions of the wearable opioid detection hair tie device.

Figure 8:
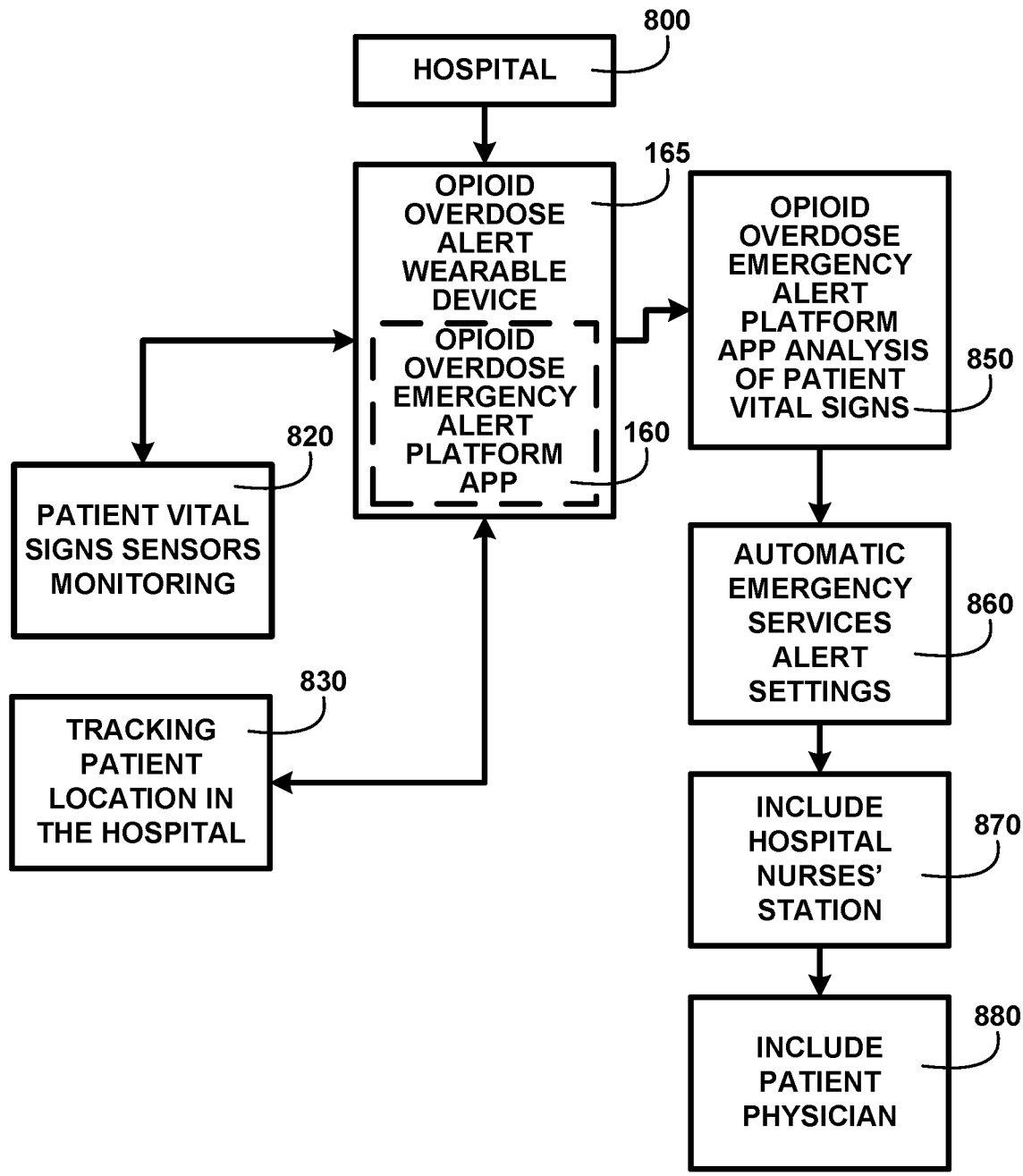
FIG. 8 shows a block diagram of an overview of hospital use of one embodiment.

Hospital Use:

FIG. 8 shows a block diagram of an overview of hospital use of one embodiment. FIG. 8 shows an opioid overdose alert wearable device 165 uses in a hospital 800 setting.

Patients wearing the opioid overdose alert wearable device 165 with the opioid overdose emergency alert platform app 160 gain the benefit of patient vital signs sensors monitoring 820. Even the hospital 800 gains by the continuous monitoring as periodic nurse checking of a patient's vital signs is not needed. Further tracking patient location in the hospital 830 facilitates reaching a patient suffering an overdose quickly. An opioid overdose emergency alert platform app analysis of patient vital signs 850 will trigger immediate automatic emergency services alert settings 860. The automatic emergency services alert settings 860 include hospital nurses' station 870 and include patient-physician 880. No delay potentially occurring with a patient lying in a bed unattended or walking for exercise down hospital halls of one embodiment.

The opioid overdose alert wearable device 165 provides the hospital staff an extension of awareness of a patient's whereabouts and condition. The GPS locator 320 of FIG. 3 for tracking a patient location 321 of FIG. 3 and physiological sensors monitor vital signs 24/7 420 of FIG. 4 transmission via the opioid overdose emergency alert platform app 160 of FIG. 1 keep the medical staff aware of the patient's condition through the continuous monitoring of the vital signs. Also, the alerts of an overdose condition will allow the medical staff to respond very quickly to an overdose condition regardless of the patient location within the hospital. The continuous GPS tracking will make the patient location within the hospital quick for the medical staff to communicate to the medical staff nearest to that location. The medical staff will be able to advise the distant medical staff of the patient's condition to alert them what immediate treatment is advisable and needed. It will also provide the medical staff some idea of where the patient was located which might point to where the patient got the overdose drugs the patient ingested or injected. The patient will also learn that even in a hospital setting the use of drugs can lead to potential overdose or critical conditions. Generally, the hospital will be the first setting in which the patient starts to become aware of the dangers of drug use because that is why they are in the hospital. If the patient continues to progress each lesson learned will reinforce what they are being told. The opioid overdose alert wearable device 165 can save their lives provided they heed the warnings for example, a drug they are about to inject contains lethal fentanyl. The drug they are about to inject has potentially lethal concentrations and impurities that could end their lives. The other lesson the patient can learn is to not trust anyone selling or providing them with drugs. For example, Fentanyl laced drugs are undetectable by sight, smell, or even taste. Therefore, the opioid overdose alert wearable device 165 becomes a vital tool for the patient in caring for themselves and recognizing the hazards confronting them in continued drug use. This will reinforce the efforts of the hospital and other medical personnel, friends, and family to help the patient realize that continued drug use could end their life.

Figure 9:
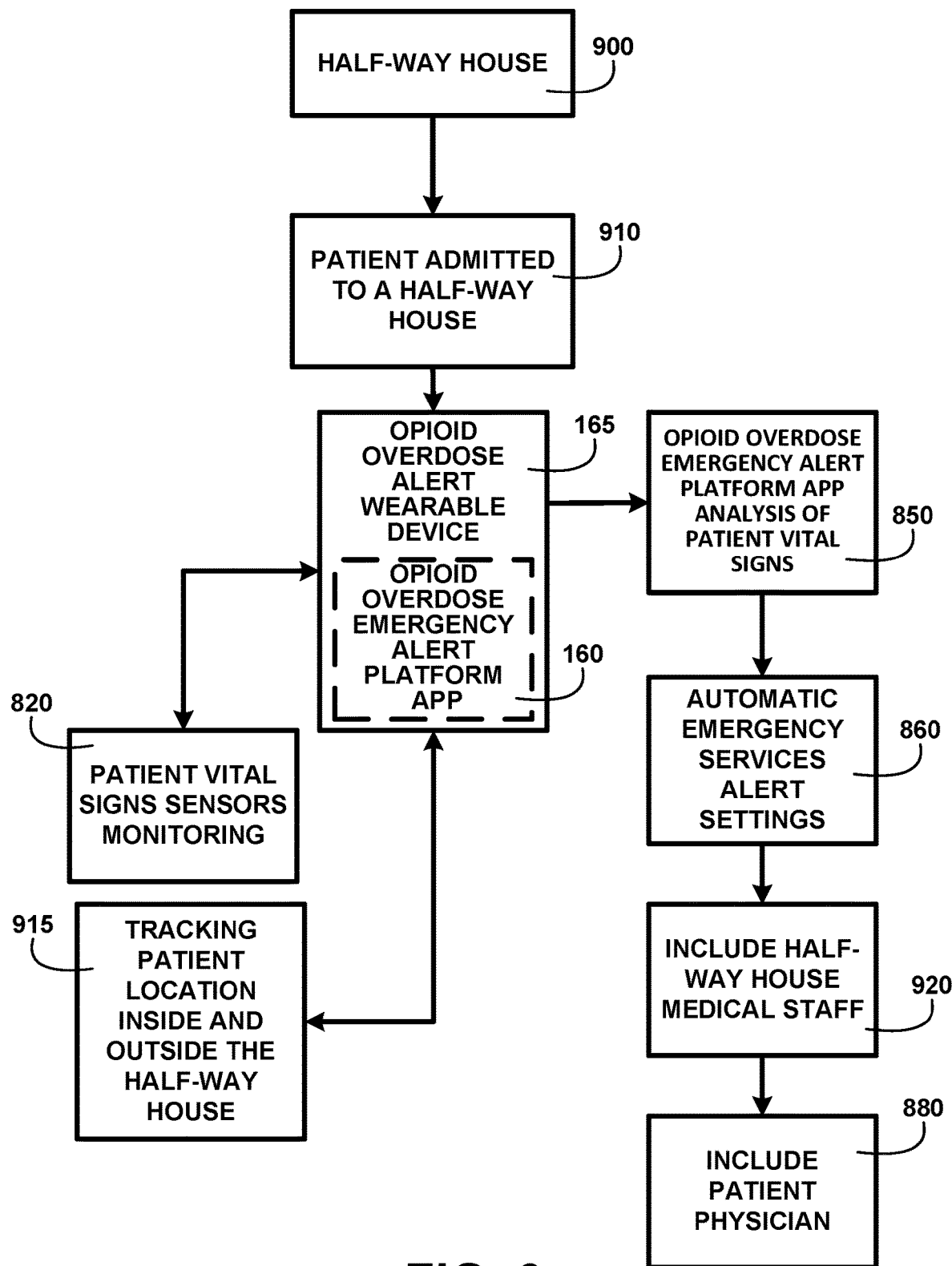
FIG. 9 shows a block diagram of an overview of the halfway house use of one embodiment.

Halfway House Use:

FIG. 9 shows a block diagram of an overview of the halfway house use of one embodiment. FIG. 9 shows a use of the opioid overdose alert wearable device 165 in a halfway house 900 setting. A patient admitted to a halfway house 910 wearing the opioid overdose alert wearable device 165 and having the opioid overdose emergency alert platform app 160 will have the benefit of patient vital signs sensors monitoring 820. A halfway house 900 setting generally allows a patient to take small trips outside the halfway house 900. The opioid overdose alert wearable device 165 provides tracking patient location inside and outside the half-way house 915. The opioid overdose emergency alert platform app analysis of patient vital signs 850 and trigger an automatic emergency services alert settings 860. The overdose alert will include halfway house medical staff 920 and include patient-physician 880 of one embodiment.

A halfway house is an institute for people with drug abuse tendencies to learn the necessary skills to reintegrate into society and better support and care for themselves. As well as serving as a residence, halfway houses provide social, medical, psychiatric, educational, and other similar services. They are termed "halfway houses" due to their being halfway between completely independent living and in-patient facilities, where residents are highly restricted in their behavior and freedoms. The opioid overdose alert wearable device 165 in a halfway house 900 setting provides a device to assist the patient from overdosing or taking lethal drugs. The opioid overdose alert wearable device 165 also assists the medical staff with early warning of an overdose condition in a patient and also alerts the medical staff of the type of drugs and frequency of use by a patient to determine their progress in ending the patient's addiction to drug use. The communications capabilities of the opioid overdose alert wearable device 165 extends the medical staff's contact with the patient from only while they are inside the halfway house to anywhere the patient may have gone outside the halfway house. The continuous GPS location monitoring of the patient also provides the halfway house staff some idea of where the patient is going which may be known by the halfway house staff to be ill-advised or even dangerous to the patient's progress in learning to care for them.

Figure 10:
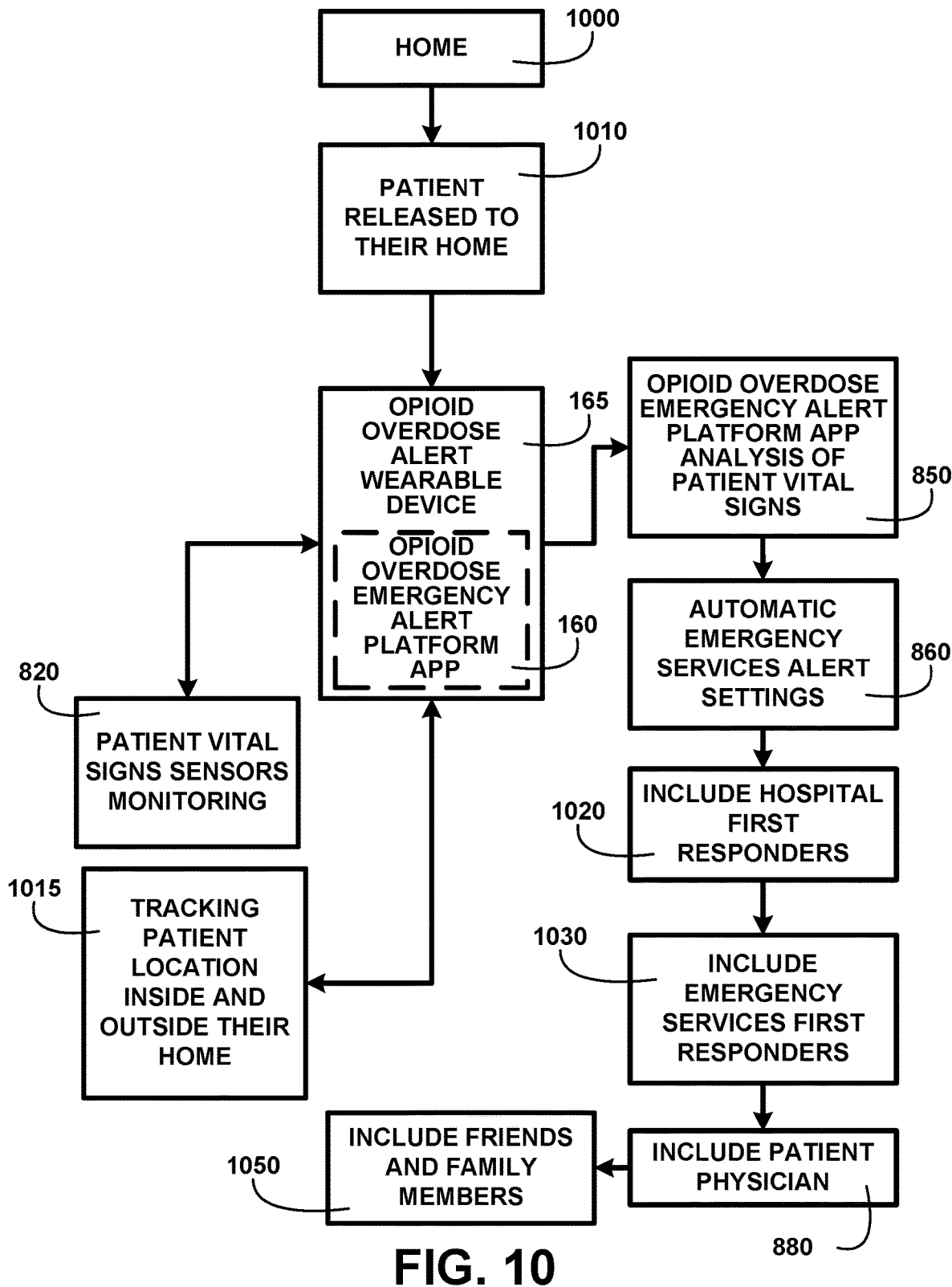
FIG. 10 shows a block diagram of an overview of home use of one embodiment.

Home Use:

FIG. 10 shows a block diagram of an overview of home use of one embodiment. FIG. 10 shows a use of the opioid overdose alert wearable device 165 in a home 1000 setting. A patient released to their home 1010 and wearing the opioid overdose alert wearable device 165 gains the benefit of the opioid overdose emergency alert platform app 160 and patient vital signs sensors monitoring 820. Home release also permits the patient to venture out of the home. Wearing the opioid overdose alert wearable device 165 provides tracking patient location inside and outside their home 1015. The opioid overdose emergency alert platform app analysis of patient vital signs 850 and automatic emergency services alert settings 860 can include hospital first responders 1020, include emergency services first responders 1030, include patient-physician 880, and include friends and family members 1050. Friends and family members may want to get training and any necessary equipment including a defibrillator, oxygen tank supply, and standby blanket to provide immediate first aid in the home due to the closer proximity to the patient of one embodiment.

A home 1000 setting for a patient can present too much opportunity for the patient to fall back on old habits related to their drug addiction. The opioid overdose alert wearable device 165 provides friends and family to track the patient's GPS location to monitor their comings and goings to determine if the patient is falling back into unadvised bad habits that may lead to an overdose condition and stall the patient's progress in ending their drug use. The opioid overdose alert wearable device 165 also provides the patient with the ability to detect if the drug they may be preparing to inject is of a poor or even lethal quality and concentration. The patient seeing the presence of fentanyl in a drug detected by the sensors of the opioid overdose alert wearable device 165 and awareness that this could be lethal may save their life. Fentanyl laced drugs are undetectable by sight, smell, or even taste. Therefore, the opioid overdose alert wearable device 165 becomes a vital tool for the patient in caring for themselves and recognizing the hazards confronting them in continued drug use. This will reinforce the efforts of medical personnel, friends, and family to help the patient come to a realization that continued drug use could end their life.

Figure 11:
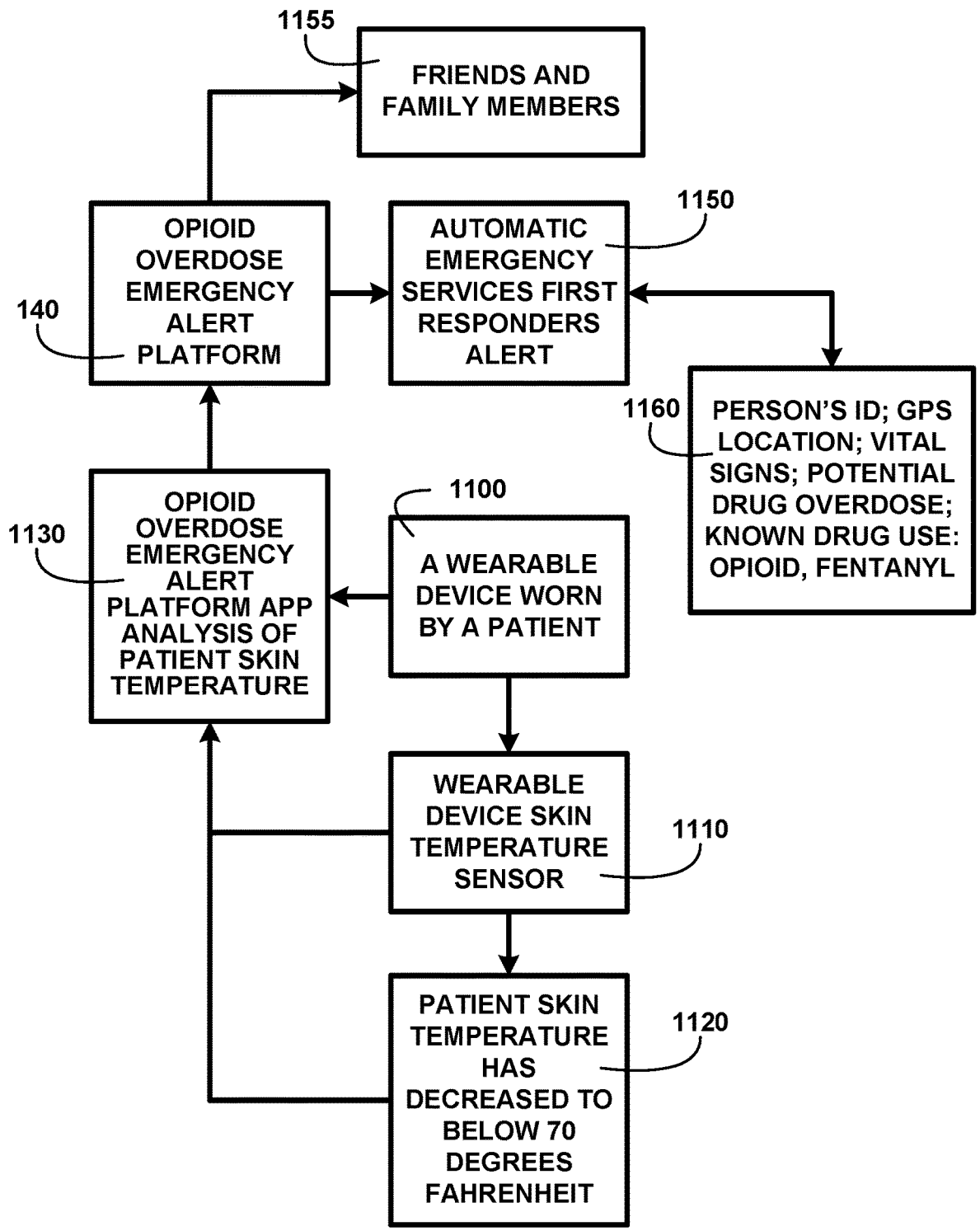
FIG. 11 shows a block diagram of an overview of friends and family members of one embodiment.

Friends and Family Members:

FIG. 11 shows a block diagram of an overview of friends and family members of one embodiment. FIG. 11 shows a wearable device worn by a patient 1100 including a wearable device skin temperature sensor 1110. The wearable device skin temperature sensor 1110 is continuously detecting and measuring the patient skin temperature. A drop in skin temperature is an indicator of a potential overdose. If a patient skin temperature has decreased to below 70 degrees Fahrenheit 1120. An opioid overdose emergency alert platform app analysis of patient skin temperature 1130 will indicate a probable overdose condition and transmit the analysis to the opioid overdose emergency alert platform 140. The opioid overdose emergency alert platform 140 transmits an automatic emergency service first responder alert 1150 including the person's ID; GPS location; vital signs; potential drug overdose; known drug use: opioid, fentanyl 1160. The alert may also be sent to friends and family members 1155 of one embodiment.

Figure 12:
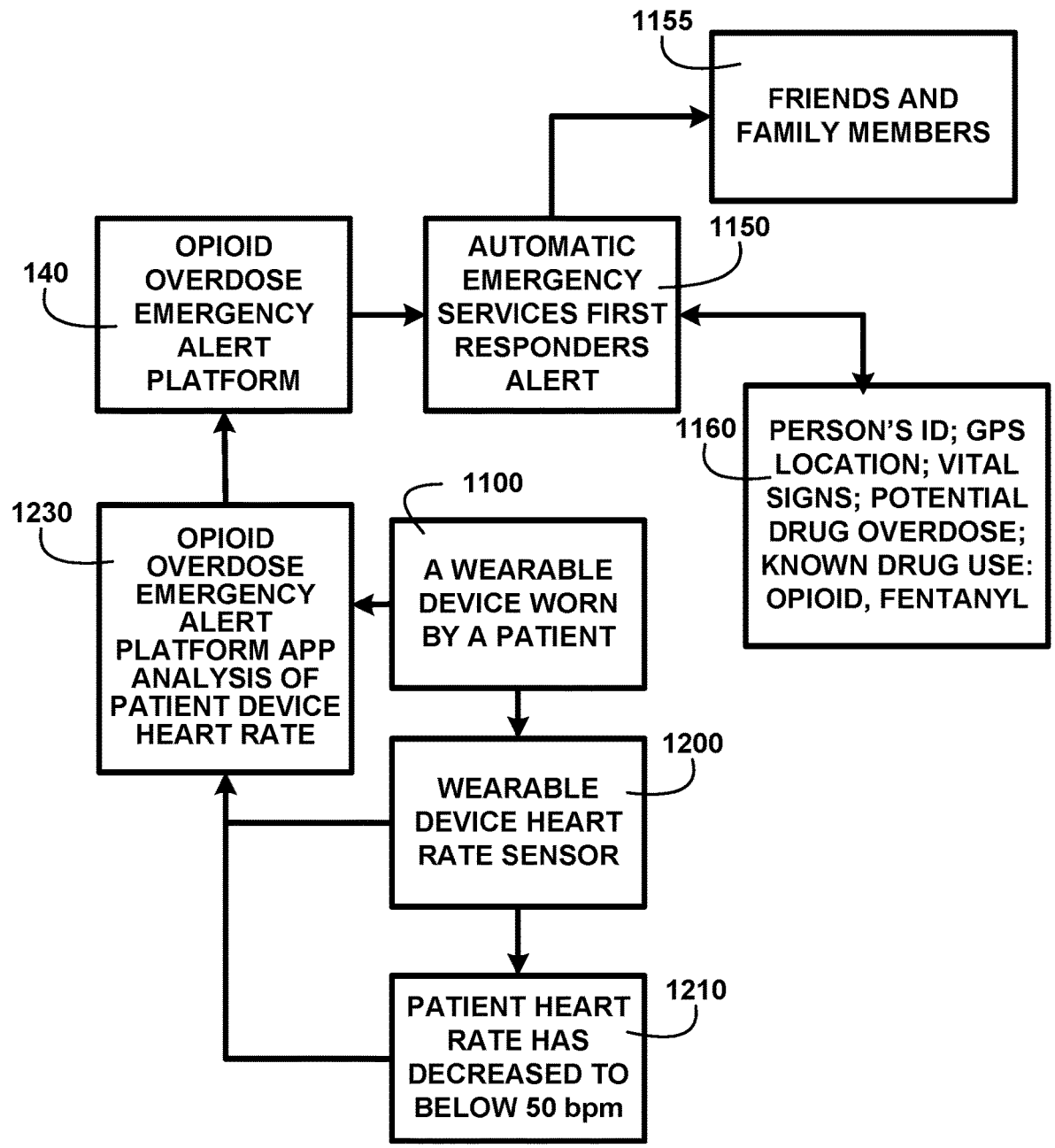
FIG. 12 shows a block diagram of an overview of a wearable device heart rate sensor of one embodiment.

Wearable Device Heart Rate Sensor:

FIG. 12 shows a block diagram of an overview of the wearable device heart rate sensor of one embodiment. FIG. 12 shows a wearable device worn by a patient 1100 that includes a wearable device heart rate sensor 1200. If a patient heart rate has decreased to below 50 bpm 1210. The low beats per minute (bpm) may in an opioid overdose emergency alert platform app analysis of patient device heart rate 1230 and a possible overdose. The opioid overdose emergency alert platform 140 will immediately broadcast an automatic emergency services first responder alert 1150. The automatic emergency services first responder alert 1150 includes the person's ID; GPS location; vital signs; potential drug overdose; known drug use: opioid, fentanyl 1160. The alert may also be sent to friends and family members 1155 who may be in closer proximity to the patient and be able to provide some level of first aid response of one embodiment.

Figure 13:
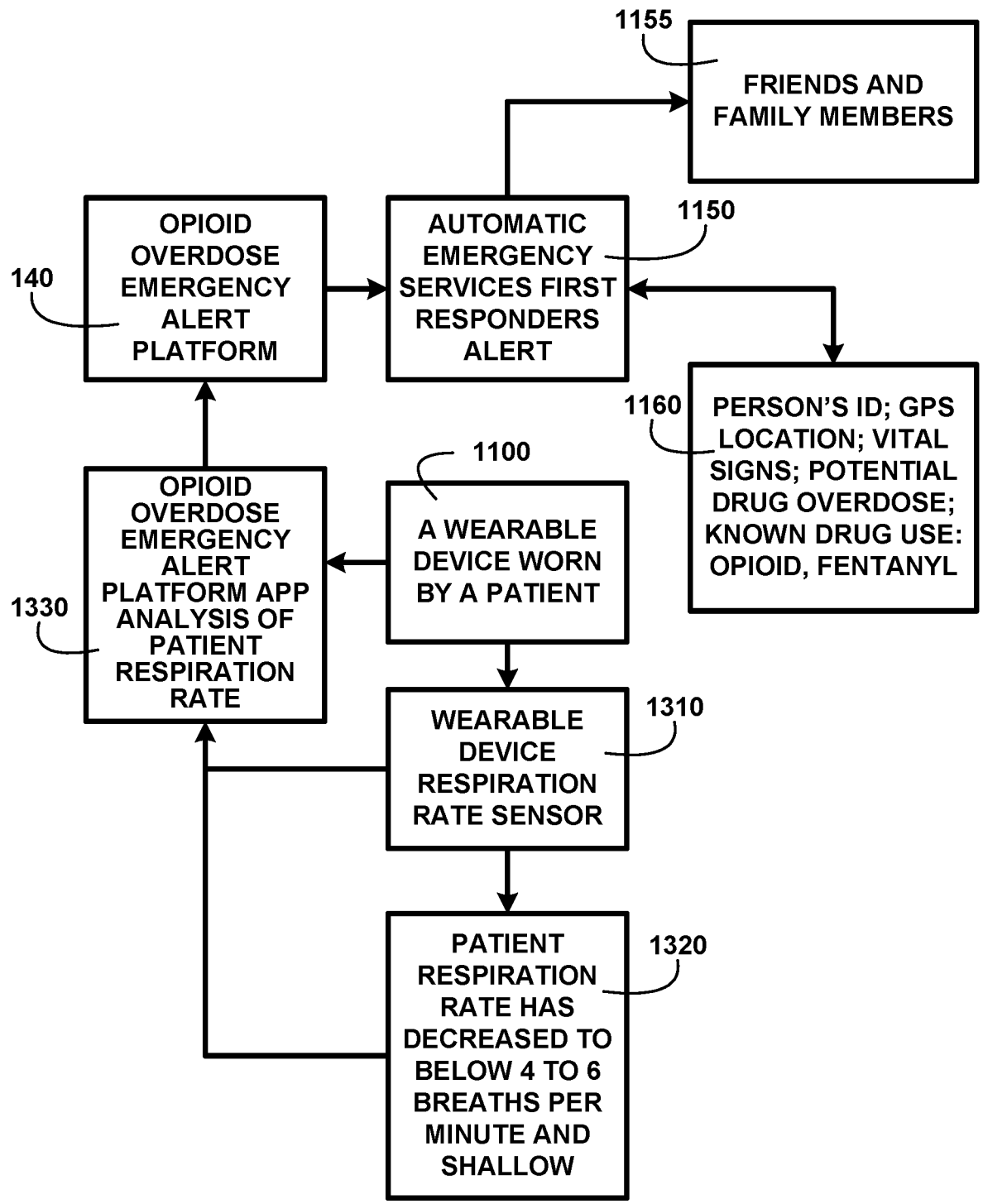
FIG. 13 shows a block diagram of an overview of a wearable device worn by a patient of one embodiment.

A Wearable Device Worn by a Patient:

FIG. 13 shows a block diagram of an overview of a wearable device worn by a patient of one embodiment. FIG. 13 shows a wearable device worn by a patient 1100. The wearable device worn by a patient 1100 includes a wearable device respiration rate sensor 1310. If a patient respiration rate has decreased to below 4 to 6 breaths per minute and shallow 1320 an opioid overdose emergency alert platform app analysis of patient respiration rate 1330 is transmitted to the opioid overdose emergency alert platform 140 to broadcast an automatic emergency services first responders' alert 1150. The automatic emergency services first responder alert 1150 includes the person's ID; GPS location; vital signs; potential drug overdose; known drug use: opioid, fentanyl 1160. The alert may also be sent to friends and family members 1155 who may be in closer proximity to the patient and be able to provide some level of first aid response of one embodiment.

Figure 14:
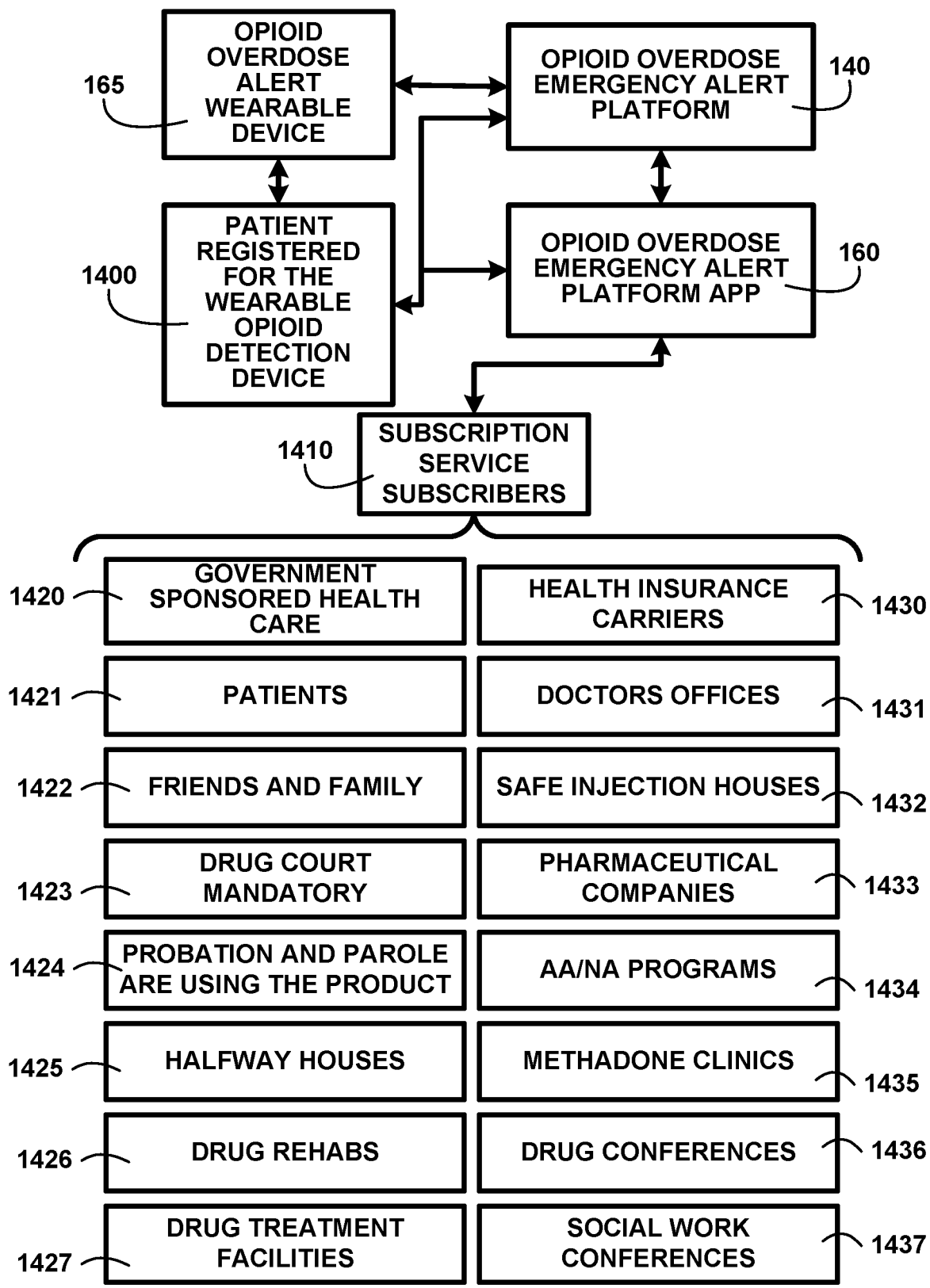
FIG. 14 shows a block diagram of an overview of the opioid overdose emergency alert platform app of one embodiment.

Opioid Overdose Emergency Alert Platform App:

FIG. 14 shows a block diagram of an overview of an opioid overdose emergency alert platform app of one embodiment. FIG. 14 shows the opioid overdose alert wearable device 165 that is wirelessly connected to the opioid overdose emergency alert platform 140 using the opioid overdose emergency alert platform app 160. A patient registered for the wearable opioid detection device 1400 also has a subscription for the use of the opioid overdose emergency alert platform app 160 to pay. The subscription may be paid by others who have an interest in reducing overdose deaths. The subscription service subscribers 1410 may include government sponsored health care 1420, patients 1421, friends and family 1422; drug court mandatory 1423, probation and parole are using the product 1424, halfway houses 1425, drug rehabs 1426, and drug treatment facilities 1427. Another group of potential subscription service subscribers 1410 may include health insurance carriers 1430, doctor's offices 1431, safe injection houses 1432, pharmaceutical companies 1433, ANNA programs 1434, methadone clinics 1435, drug conferences 1436, and social work conferences 1437 of one embodiment.

Figure 15:
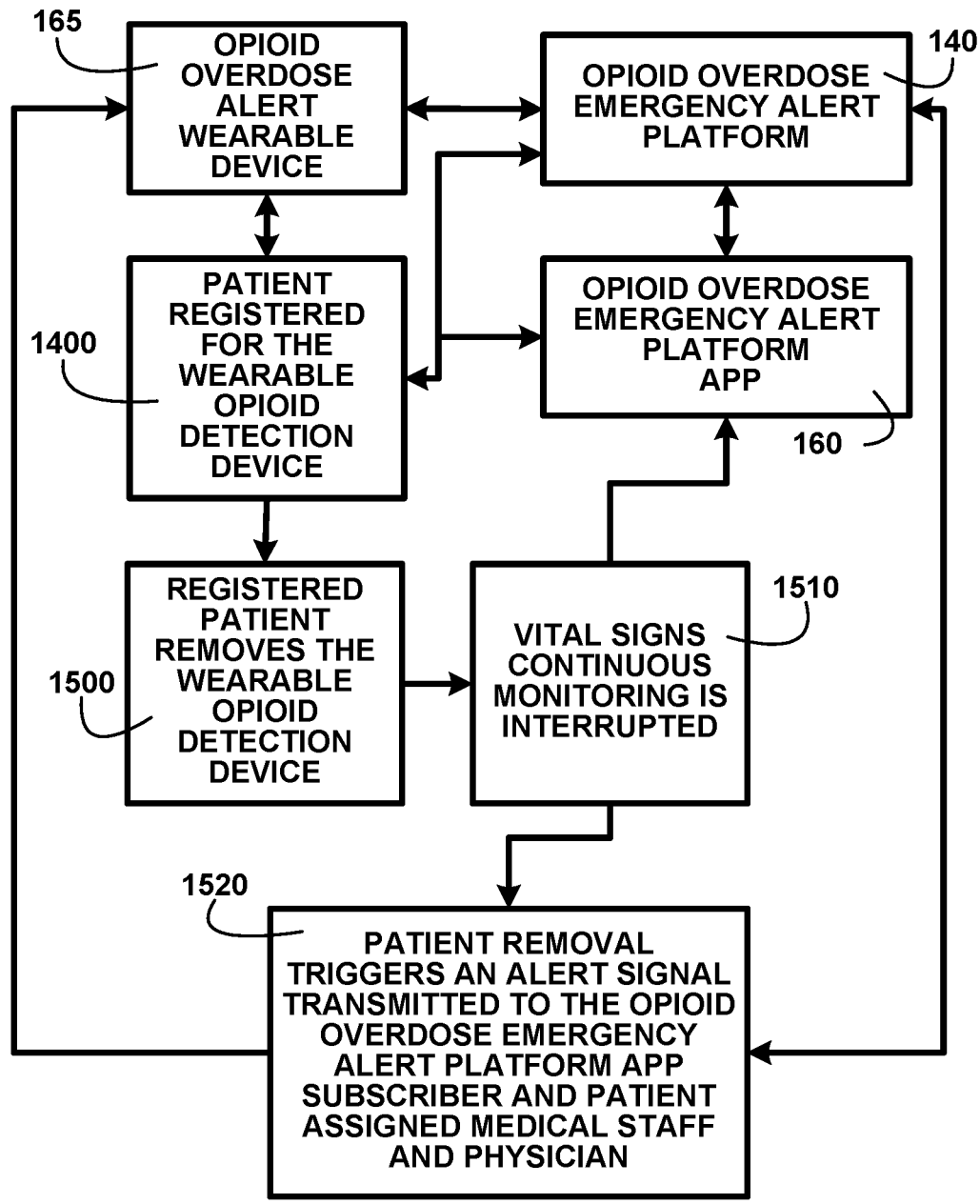
FIG. 15 shows a block diagram of an overview of vital signs continuous monitoring interrupted of one embodiment.

Vital Skins Continuous Monitoring Interrupted:

FIG. 15 shows a block diagram of an overview of vital signs continuous monitoring interrupted of one embodiment. FIG. 15 shows the opioid overdose alert wearable device 165 that is wirelessly connected to the opioid overdose emergency alert platform 140 using the opioid overdose emergency alert platform app 160. A patient registered for the wearable opioid detection device 1400 is supposed to wear the opioid overdose alert wearable device 165 continuously to get the overdose alerts to perhaps save their life. When a registered patient removes the wearable opioid detection device 1500 the vital signs continuous monitoring is interrupted 1510. The interruption of the vital signs continuous monitoring due to the patient removal triggers an alert signal transmitted to the opioid overdose emergency alert platform app subscriber and patient assigned medical staff and physician 1520. The subscriber and patient assigned medical staff and physician can contact the patient to why the opioid overdose alert wearable device 165 was removed and advise the patient to immediately start wearing the opioid overdose alert wearable device 165 of one embodiment.

The opioid overdose alert wearable device 165 can be worn while the patient is for example, showering. The components are sealed to prevent damage by incidental exposure to a moderate amount of water including rain. This means the opioid overdose alert wearable device 165 can be worn continuously by the patient and maintain the 24/7 monitoring of vital signs and GPS location. Once the patient has experienced the benefits of alerts and early warnings on their drug use the patient will not want to take off the opioid overdose alert wearable device 165. When the patient understands the opioid overdose alert wearable device 165 may be the only salvation they have in an overdose condition and help them in detecting potentially lethal drugs they will realize the opioid overdose alert wearable device 165 is in the true meaning their "life-line" while they continue with drug use.

Figure 16A:
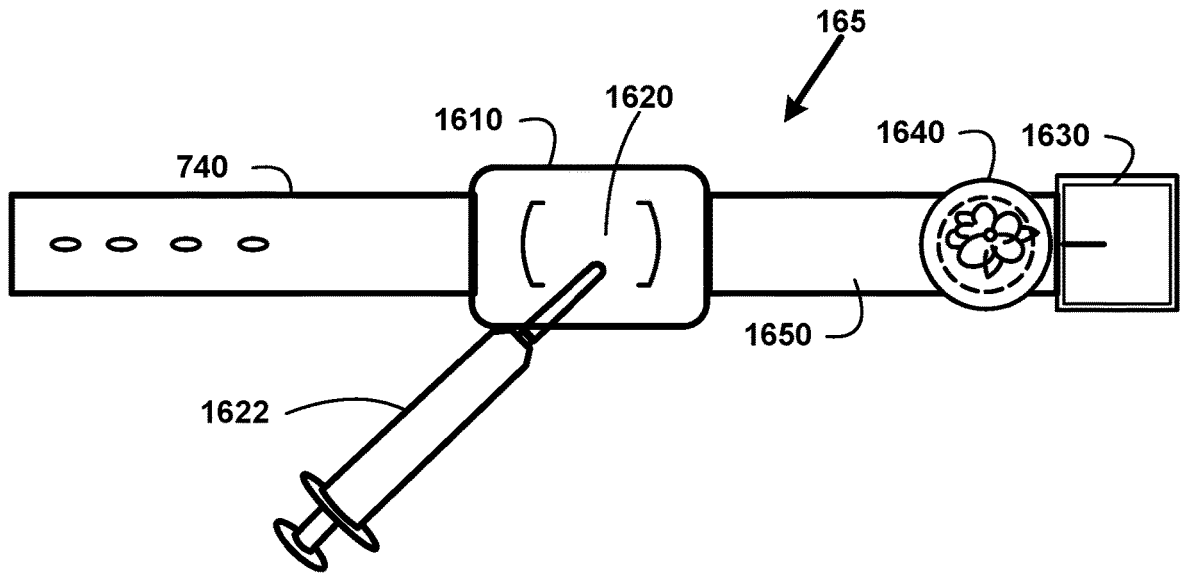
FIG. 16A shows for illustrative purposes only an example of fentanyl concentration of one embodiment.

Fentanyl Concentration:

FIG. 16A shows for illustrative purposes only an example of fentanyl concentration of one embodiment. FIG. 16A shows the opioid overdose alert wearable device 165 with a wrist band 740 and the front face of wearable opioid detection device 1610. In one embodiment the opioid overdose alert wearable device 165 includes a cooker 1620 in which the patient cooks the drug to be injected into a liquid for drawing into an injection syringe 1622. The opioid overdose alert wearable device 165 with a wrist band 740 includes a wrist band clasp 1630, logo 1640, and band 1650 of one embodiment.

This may seem counter-productive by providing a cooker for the patient to prepare and inject drugs. The typical tool is a spoon. However, a spoon does not include sensors such as those coupled to the opioid overdose alert wearable device 165. The sensors are further described in FIG. 16B detecting what the drug actually is and if it contains for example, lethal Fentanyl. Fentanyl laced drugs are undetectable by sight, smell, or even taste. Therefore, the opioid overdose alert wearable device 165 becomes a vital tool for the patient in caring for themselves and recognizing the hazards confronting them in continued drug use.

Figure 16B:
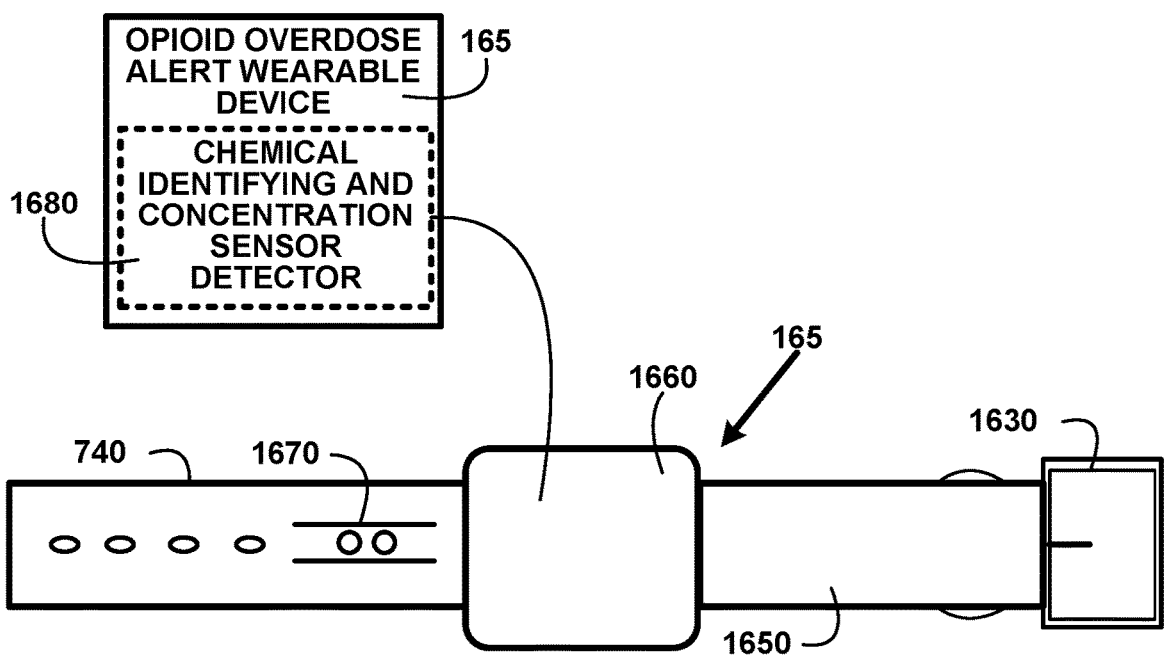
FIG. 16B shows for illustrative purposes only an example of chemical identifying and concentration sensor detector of one embodiment.

Chemical Identifying and Concentration Sensor Detector:

FIG. 16B shows for illustrative purposes only an example of chemical identifying and concentration sensor detector of one embodiment. FIG. 16B shows an opioid overdose alert wearable device 165 including a wrist band 740, wrist band clasp 1630, and band 1650. Also shown is the back face of wearable opioid detection device 1660. The back faces 1680 of the opioid overdose alert wearable device 165 with at least one chemical identifying and concentration sensor detector. In one embodiment, the opioid overdose alert wearable device 165 includes in the band sensor results indicator lights to alert the patient of the drug ID and potentially dangerous concentrations 1670.

Figure 17A:
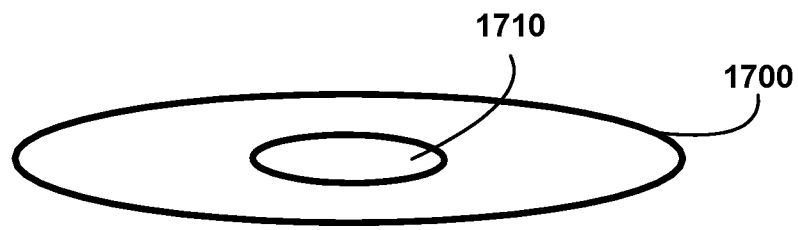
FIG. 17A shows for illustrative purposes only an example of cooker bottom of one embodiment.

Cooker Bottom:

FIG. 17A shows for illustrative purposes only an example of cooker bottom of one embodiment. FIG. 17A shows a cooker bottom 1700 that includes a cooker sensor contact area 1710. The cooker sensor contact area 1710 exposes the sensors to the drug liquid and fumes for analysis to identify the drug and measure the concentration of one embodiment. The cooker sensor contact area 1710 provides a contact vehicle for the fumes of cooking drugs to come in contact with the detection sensors. The sensors sample the fumes and perform a detection analysis to identify the drug(s) and any other components the patient was not aware of for example, Fentanyl. Through this process, the opioid overdose alert wearable device 165 also becomes an early warning system to prevent an overdose condition before the injection of drugs actually causes an overdose condition.

Figure 17B:
FIG. 17B shows for illustrative purposes only an example of a cooker tray of one embodiment.

Cooker Tray:

FIG. 17B shows for illustrative purposes only an example of a cooker tray of one embodiment. FIG. 17B shows a cooker drug liquid tray 1720 where a patient cooks the drug they are planning to inject. The cooker drug liquid tray 1720 provides sufficient heat to liquefy solid or pasty materials of one embodiment. There is at least one chemical identifying and concentration sensor detector coupled to the opioid overdose alert wearable device 165 analyses and detects the actual chemicals from the fumes of the cooking drug. The analysis and detection identification are quick and accurate. This provides the information the patient needs to proceed or not and discard potential lethal drugs and dangerous concentrations. The opioid overdose alert wearable device 165 makes the patient's awareness of any dangers easier to ascertain through the use of cooker indication lights as described further in FIG. 17C.

Figure 17C:
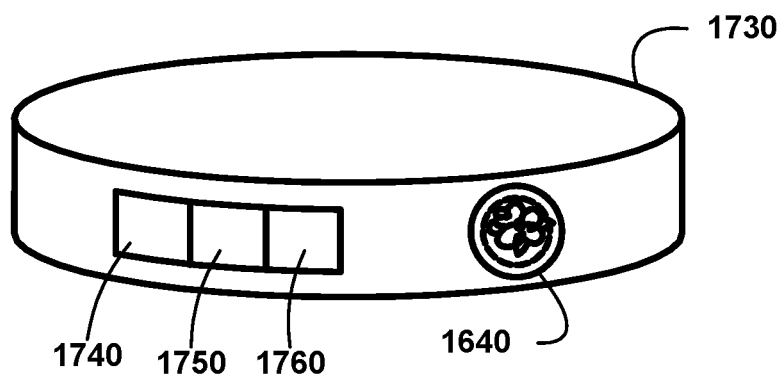
FIG. 17C shows for illustrative purposes only an example of cooker indication lights of one embodiment.

Cooker Indication Lights:

FIG. 17C shows for illustrative purposes only an example of cooker indication lights of one embodiment. FIG. 17C shows a cooker assembly 1730 with the logo 1640 attached. The cooker assembly 1730 has mounted on the exterior a set of sensor detector indicator lights to provide a warning to the patient if the drug they are about to inject has a dangerous drug identified and dangerous concentrations that could be lethal.

A drug chemical identifying and concentration sensor detector indicator light green 1740 indicates the drug, although all are dangerous, is not necessarily lethal or at a lethal concentration. A drug chemical identifying and concentration sensor detector indicator light yellow 1750 alerts the patient the drug may be at dangerous concentrations. A drug chemical identifying and concentration sensor detector indicator light red 1760 is a serious alert warning that the drug is lethal including fentanyl and at a lethal concentration level. The patient must heed these alerts to avoid an overdose or death of one embodiment.

A patient will become accustomed to referring to the drug chemical identifying and concentration sensor detector indicator lights before injecting a drug. This will reduce the chance of an overdose and injecting a lethal drug component or concentration. This may lead to a reduction in the number of lethal drugs being injected, leading to a decrease in drug deaths and overdoses. In this way, the opioid overdose alert wearable device 165 provides additional benefits to the patient as an education tool. The greater the number the patient encounters of potentially lethal drugs the patient will understand without the opioid overdose alert wearable device 165 they are playing Russian roulette with every injection they take. This may lead to a sense of understanding that they, themselves, have the capability of making correct decisions to care for themselves. This will contribute to their progress to their power of self-determination regarding their continued drug use. While many people will have told them of the dangers of drug use, self-awareness and coming to a self-realization of the dangers of drug use confronting them will empower them to better form the decision to stop.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. An opioid overdose alert system, comprising:
   a wearable device having physiological sensors, the wearable device configured to be worn by a user to continuously monitor vital signs of the user;
   a chemical sensor coupled to the wearable device configured to identify and measure concentration levels of a predetermined drug that includes fentanyl and to determine if a predetermined level of fentanyl exists as a lethal concentration levels;
   a global positioning location device coupled to the wearable device configured to continuously track a physical geographical location of the user;
   an alert signaling device coupled to the wearable device and chemical sensor and configured to receive the lethal concentration level; and
   a transmitter coupled to the alert signaling device and global positioning location device configured to automatically alert the user and a designated remote user of potential lethal overdosing based on the lethal concentration level and to transmit the vital signs and the physical geographical location of the user to the designated remote user.

2. The opioid overdose alert system of claim 1, wherein the transmitter is configured to automatically send the lethal concentration level and the vital signs and the physical geographical location of the user to an emergency first responder.

3. The opioid overdose alert system of claim 1, wherein the physiological sensors include sensors configured to detect skin temperature, heart rate and respiration rate.

4. The opioid overdose alert system of claim 3, wherein the transmitter is further configured to automatically transmit the lethal concentration level, the skin temperature, the heart rate, and the respiration rate to the designated remote user.

5. The opioid overdose alert system of claim 4, wherein the transmitter is further configured to automatically send the skin temperature, the heart rate, the respiration rate, the vital signs and the physical geographical location of the user to an emergency first responder.

6. The opioid overdose alert system of claim 1, further comprising a training module having interactive immediate first aid instructions for the user and the designated remote user.

7. The opioid overdose alert system of claim 1, further comprising a cellular service device coupled to the wearable device configured to automatically transmit the potential lethal overdosing based on the lethal concentration level, the vital signs and the physical geographical location of the user to the designated remote user via cellular transmission.

8. An opioid overdose alert system, comprising:
a wearable device having physiological sensors, the wearable device configured to be worn by a user to continuously monitor vital signs of the user;
a chemical sensor coupled to the wearable device configured to identify and measure concentration levels of a predetermined drug that includes fentanyl and to determine if a predetermined level of fentanyl exists as a lethal concentration level;
a global positioning location device coupled to the wearable device configured to continuously track a physical geographical location of the user;
an alert signaling device coupled to the wearable device and chemical sensor and configured to receive the lethal concentration level;
a transmitter coupled to the alert signaling device and global positioning location device configured to automatically alert the user and a designated remote user of potential lethal overdosing based on the lethal concentration level and to transmit the vital signs and the physical geographical location of the user to the designated remote user; and
a cellular service device coupled to the wearable device configured to automatically transmit the potential lethal overdosing based on the lethal concentration level, the vital signs and the physical geographical location of the user to the designated remote user via cellular transmission.

9. The opioid overdose alert system of claim 8, wherein the transmitter is configured to automatically send the lethal concentration level and the vital signs and the physical geographical location of the user to an emergency first responder.

10. The opioid overdose alert system of claim 8, wherein the physiological sensors include sensors configured to detect skin temperature, heart rate and respiration rate.

11. The opioid overdose alert system of claim 8, further comprising a training module having interactive immediate first aid instructions for the user and the designated remote user.

12. The opioid overdose alert system of claim 10, wherein the transmitter is further configured to automatically transmit the lethal concentration level, the skin temperature, the heart rate, and the respiration rate to the designated remote user.

13. The opioid overdose alert system of claim 12, wherein the transmitter is further configured to automatically send the skin temperature, the heart rate, the respiration rate, the vital signs and the physical geographical location of the user to an emergency first responder.

14. The opioid overdose alert system of claim 8, further comprising a mobile device having an opioid application operating on the mobile device and being coupled to the wearable device and configured to display the vital signs, the measured concentration levels, and the lethal concentration level.

15. An opioid overdose alert system, comprising:
a wearable device having physiological sensors, the wearable device configured to be worn by a user to continuously monitor vital signs, skin temperature, heart rate and respiration rate;
a chemical sensor coupled to the wearable device configured to identify and measure concentration levels of a predetermined drug that includes fentanyl and to determine if a predetermined level of fentanyl exists as a lethal concentration level;
a global positioning location device coupled to the wearable device configured to continuously track a physical geographical location of the user;
an alert signaling device coupled to the wearable device and chemical sensor and configured to receive the lethal concentration level;
a transmitter coupled to the alert signaling device and global positioning location device configured to automatically alert the user and a designated remote user of potential lethal overdosing based on the lethal concentration level and to transmit the vital signs, the skin temperature, the heart rate, the respiration rate and the physical geographical location of the user to the designated remote user; and
a cellular service device coupled to the wearable device configured to automatically transmit the potential lethal overdosing based on the lethal concentration level, the vital signs, the skin temperature, the heart rate, the respiration rate and the physical geographical location of the user to the designated remote user via cellular transmission.

16. The opioid overdose alert system of claim 15, wherein the transmitter is configured to automatically send the lethal concentration level and the vital signs and the physical geographical location of the user to an emergency first responder.

17. The opioid overdose alert system of claim 14, further comprising a training module having interactive immediate first aid instructions for the user and the designated remote user.

18. The opioid overdose alert system of claim 14, wherein the transmitter is further configured to automatically send the skin temperature, the heart rate, the respiration rate, the vital signs and the physical geographical location of the user to an emergency first responder.

19. The opioid overdose alert system of claim 14, further comprising a mobile device having an opioid application operating on the mobile device and being coupled to the wearable device and configured to display the vital signs, the measured concentration levels, and the lethal concentration level.

20. The opioid overdose alert system of claim 14, wherein the physiological sensors include an oxygen saturation sensor configured to continuously monitor and measure oxygen saturation levels.

\* \* \* \* \*